(12) United States Patent
Kalis et al.

(10) Patent No.: US 11,068,824 B1
(45) Date of Patent: Jul. 20, 2021

(54) AUTOMATIC ANALYSIS OF PROCESS AND/OR OPERATIONS DATA FOR CHANNEL OPTIMIZATION

(71) Applicant: Accenture Global Solutions Limited, Dublin (IE)

(72) Inventors: Brian P. Kalis, Savage, MN (US); Jean-Pierre Stephan, Sewickley, PA (US); Jeff Willihnganz, Medina, MN (US)

(73) Assignee: Accenture Global Solutions Limited, Dublin (IE)

( * ) Notice: Subject to any disclaimer, the term of this patent is extended or adjusted under 35 U.S.C. 154(b) by 463 days.

(21) Appl. No.: 15/684,631

(22) Filed: Aug. 23, 2017

Related U.S. Application Data

(60) Provisional application No. 62/517,622, filed on Jun. 9, 2017.

(51) Int. Cl.
  *G06Q 10/06* (2012.01)
  *G06Q 30/02* (2012.01)

(52) U.S. Cl.
  CPC ..... *G06Q 10/0637* (2013.01); *G06Q 30/0201* (2013.01)

(58) Field of Classification Search
  CPC .................. G06Q 10/0637; G06Q 30/0201
  USPC ....................................................... 705/7.29
  See application file for complete search history.

(56) References Cited

U.S. PATENT DOCUMENTS

| | | | |
|---|---|---|---|
| 8,352,608 B1* | 1/2013 | Keagy ................... | G06F 8/63 709/226 |
| 2012/0020473 A1* | 1/2012 | Mart ...................... | H04L 51/14 379/265.09 |
| 2012/0116800 A1* | 5/2012 | McCallie ............... | G16H 40/67 705/2 |
| 2017/0017971 A1* | 1/2017 | Moreau .............. | G06Q 30/0202 |

OTHER PUBLICATIONS

NICE Introduces Total Voice of the Customer, Combining Surveys with Interaction Analytics, PR Newswire, Feb. 8, 2016 (Year: 2016).*

* cited by examiner

*Primary Examiner* — Charles Guiliano
(74) *Attorney, Agent, or Firm* — Harrity & Harrity, LLP

(57) ABSTRACT

A device may receive data associated with customers, a customer-related process, or customer-related operations of an organization. The device may process the data using a technique. The device may map the data to an organization operating model. The organization operating model may be used to perform an analysis to identify a deficiency related to the customers, the customer-related process, or the customer-related operations, or a first manner in which to improve a customer-channel combination, the customer-related process, or the customer-related operations. The device may perform the analysis of the data. The device may identify the customer-channel combination of the organization. The customer-channel combination may identify a channel via which the organization acquires, engages, or retains the customers. The device may perform an action to positively impact performance of the customer-related process, to positively impact the customer-related operations, or to modify the customer-channel combination of the organization.

20 Claims, 16 Drawing Sheets

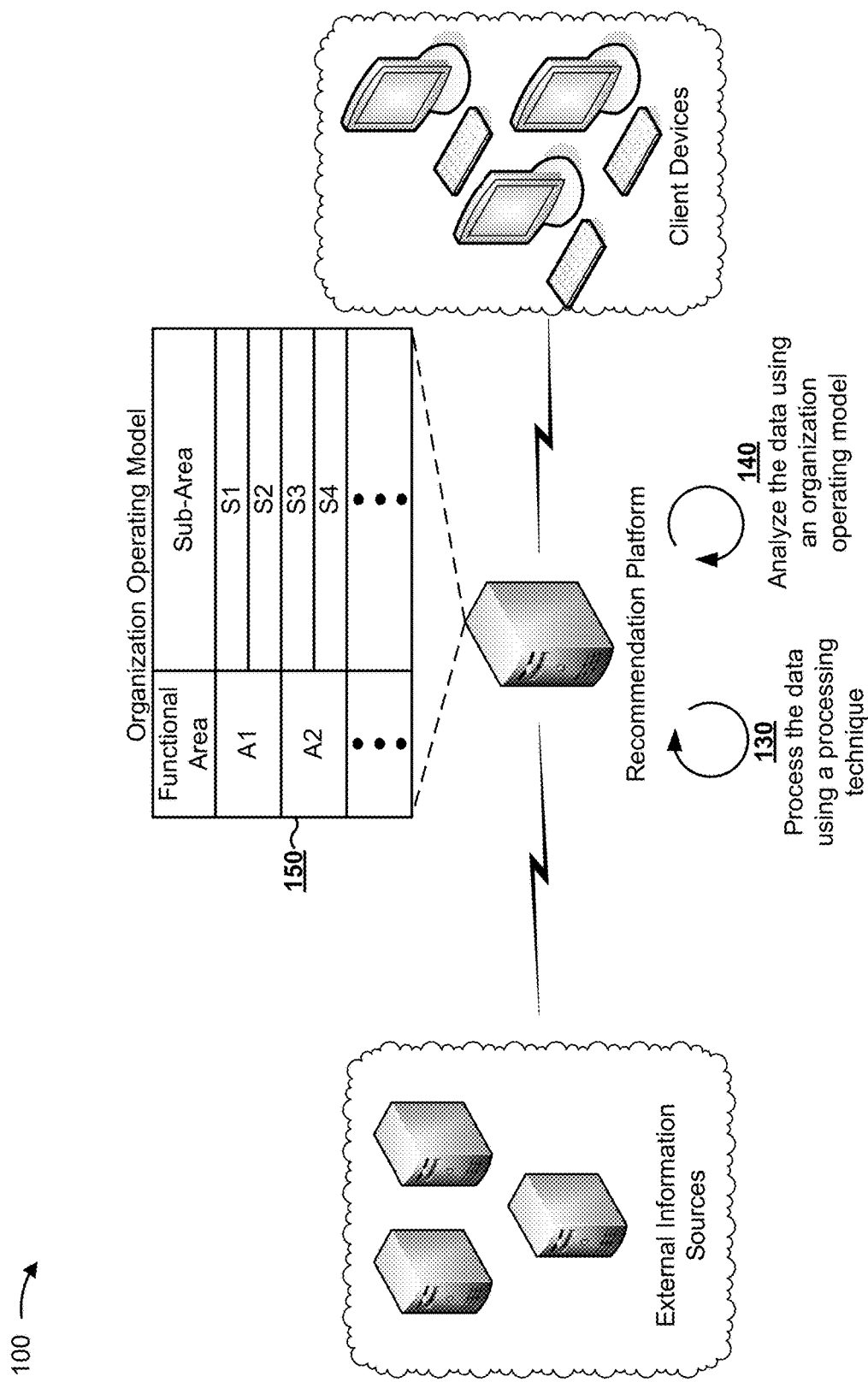

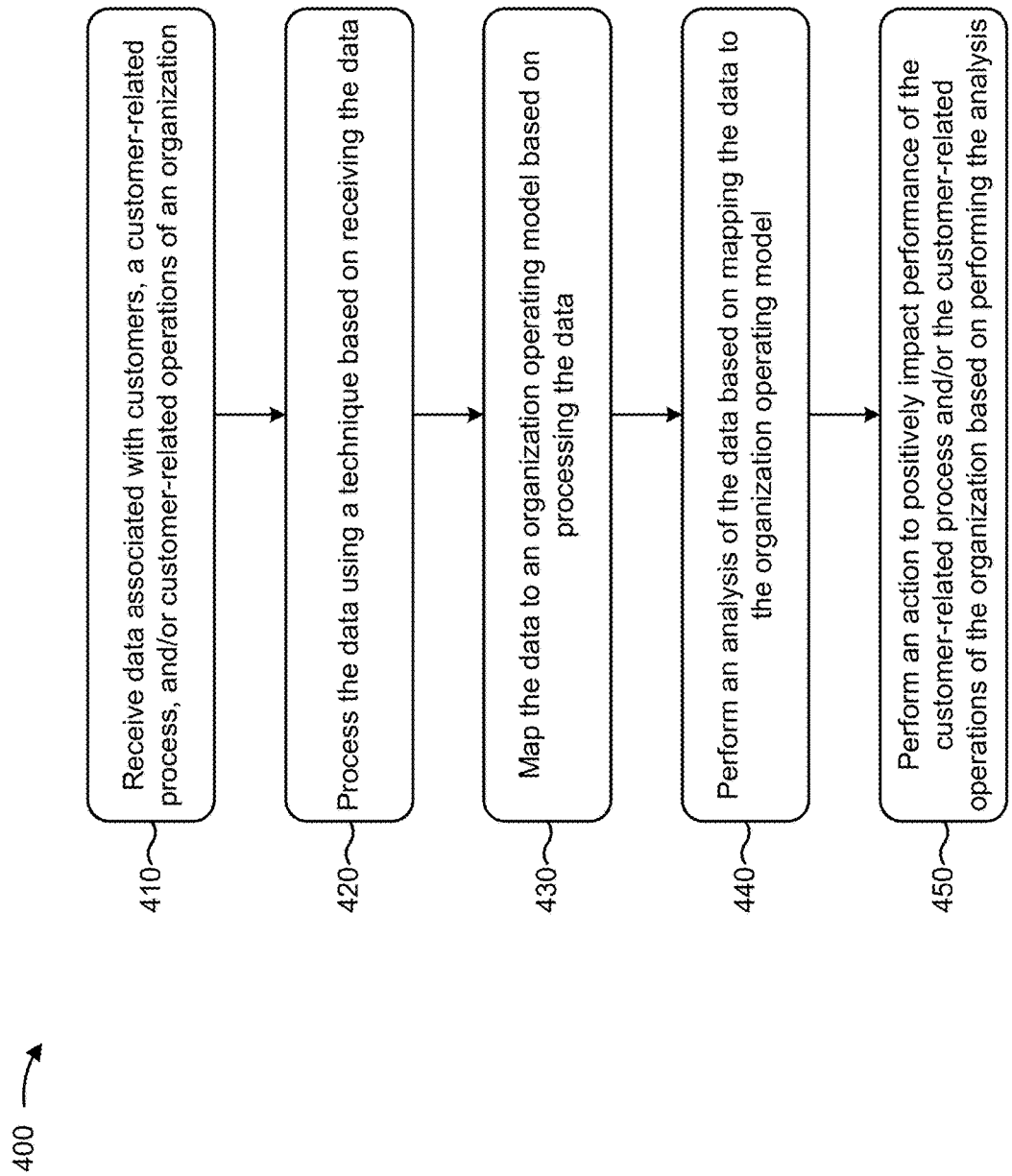

AUTOMATIC ANALYSIS OF PROCESS AND/OR OPERATIONS DATA FOR CHANNEL OPTIMIZATION

RELATED APPLICATION(S)

This application claims priority under 35 U.S.C. § 119 to U.S. Provisional Patent Application No. 62/517,622, filed on Jun. 9, 2017, the content of which is incorporated by reference herein in its entirety.

BACKGROUND

A process may include a set of interrelated activities that interact to achieve a result. For example, an organization may implement a process related to obtaining customers, retaining customers, engaging customers, and/or the like. A result of the process may be affected by a structure and/or order of the process and/or the organization.

SUMMARY

According to some possible implementations, a device may include one or more processors to receive data associated with customers, a customer-related process, or customer-related operations of an organization. The data may be received from an external information source. The one or more processors may process the data using a technique after receiving the data. The technique may be used to identify at least one of a trend related to the customers of the organization, or a deficiency related to the customer-related process or the customer-related operations. The one or more processors may map the data to an organization operating model based on processing the data. The organization operating model may be used to identify the trend or the deficiency. The one or more processors may perform an analysis of the data based on mapping the data to the organization operating model. The one or more processors may identify a customer-channel combination of the organization based on performing the analysis. The customer-channel combination may be related to a manner in which the organization acquires, engages, or retains the customers. The one or more processors may perform an action to positively impact performance of the customer-related process, to positively impact the customer-related operations, or to modify the customer-channel combination of the organization.

According to some possible implementations, a method may include receiving, by a device, data associated with customers, a customer-related process, or customer-related operations of an organization. The method may include processing, by the device, the data using a technique after receiving the data. The technique may include natural language processing. The method may include mapping, by the device, the data to an organization operating model based on processing the data. The organization operating model may be used to perform an analysis of the data to identify at least one of a deficiency related to the customers, the customer-related process, or the customer-related operations of the organization, or a first manner in which to improve a customer-channel combination, the customer-related process, or the customer-related operations. The method may include performing, by the device, the analysis of the data based on mapping the data to the organization operating model. The method may include identifying, by the device, the customer-channel combination of the organization based on performing the analysis. The customer-channel combination may identify a channel via which the organization acquires, engages, or retains the customers. The method may include performing, by the device, an action to positively impact performance of the customer-related process, to positively impact the customer-related operations, or to modify the customer-channel combination of the organization.

According to some possible implementations, a non-transitory computer-readable medium may store one or more instructions that, when executed by one or more processors, cause the one or more processors to receive data associated with customers, one or more customer-related processes, or one or more customer-related operations of one or more organizations. The data may include cross-industry or multi-domain data. The one or more instructions, when executed by the one or more processors, may cause the one or more processors to process the data using one or more techniques after receiving the data. The one or more techniques may permit the data to be mapped to one or more organization operating models. The one or more instructions, when executed by the one or more processors, may cause the one or more processors to map the data to the one or more organization operating models based on processing the data. The one or more organization operating models may be related to one or more other organizations. The one or more organization operating models may identify one or more functional areas or one or more sub-areas related to the one or more other organizations.

The one or more instructions, when executed by the one or more processors, may cause the one or more processors to perform one or more analyses of the data based on mapping the data to the one or more organization operating models. The one or more analyses may relate to one or more customer-channel combinations of the one or more organizations. The one or more instructions, when executed by the one or more processors, may cause the one or more processors to identify the one or more customer-channel combinations of the one or more organizations to determine whether to modify the one or more customer-channel combinations based on performing the one or more analyses. The one or more customer-channel combinations may be related to the customers, the one or more customer-related processes, or the one or more customer-related operations of the one or more organizations. The one or more instructions, when executed by the one or more processors, may cause the one or more processors to perform one or more actions to positively impact performance of the one or more customer-related processes, to positively impact the one or more customer-related operations, or to modify the one or more customer-channel combinations of the one or more organizations.

BRIEF DESCRIPTION OF THE DRAWINGS

FIGS. 1A-1D are diagrams of an overview of an example implementation described herein;

FIG. 4 is a flow chart of an example process for automatic analysis of process and/or operations data for channel optimization;

DETAILED DESCRIPTION

The following detailed description of example implementations refers to the accompanying drawings. The same reference numbers in different drawings may identify the same or similar elements.

An organization may implement a process to perform a function of the organization. For example, the organization may implement a process to perform customer acquisition, customer retention, customer engagement, and/or the like. The organization may lack a technique for efficiently and accurately performing a computer-based analysis of a performance of the process and/or the organization. In addition, the organization may lack a technique for comparing the performance of the process and/or operations of the organization to a threshold (e.g., a benchmark, an industry standard, an organization identified as a high-performing healthcare organization relative to other healthcare organizations), such as to identify a deficiency related to the performance, to improve performance of the process, and/or the like.

Implementations described herein provide a recommendation platform that is capable of receiving data associated with a performance of a process of an organization and/or operations of the organization, analyzing the data to identify a deficiency related to the performance of the process and/or operations and/or a manner in which to improve the performance, and/or automatically performing an action to positively impact the deficiency and/or to improve the performance.

In this way, the recommendation platform increases an efficiency of analyzing a process of an organization and/or operations of the organization. In addition, the recommendation platform improves an accuracy of a result and/or output of a process, thereby conserving processing resources that would otherwise be consumed due to inaccurate results and/or outputs. Further, the recommendation platform improves performance of a process and/or operations of an organization, thereby conserving processing resources and/or computing resources of devices used to implement the process and/or the operations.

FIGS. 1A-1D are diagrams of an overview of an example implementation 100 described herein. As shown in FIGS. 1A-1D, example implementation 100 includes one or more external information sources, a recommendation platform, and one or more client devices.

Figure 1A:
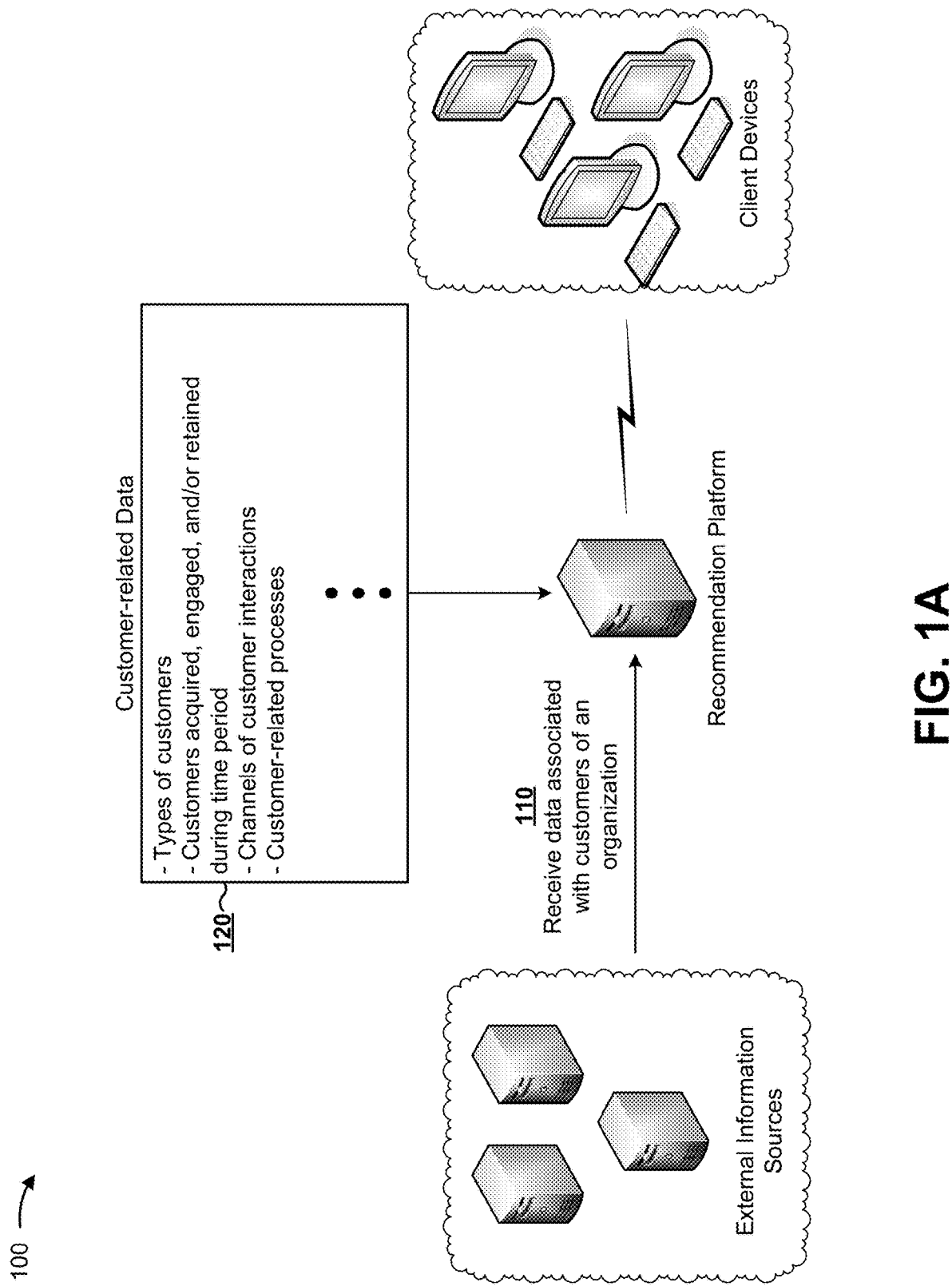

As shown in FIG. 1A, and by reference number 110, the recommendation platform may receive, from the external information sources, data associated with customers of an organization (e.g., customer-related data). For example, and as shown by reference number 120, the data received may relate to the types of customers of the organization, information associated with customers acquired, engaged, and/or retained during a time period, channels via which customers interact with the organization, customer-related processes of the organization, and/or the like. In some implementations, the recommendation platform may receive millions, billions, trillions, etc. of data elements when receiving the data.

As shown in FIG. 1B, and by reference number 130, the recommendation platform may process the data using a processing technique. For example, the recommendation platform may process the data using natural language processing, artificial intelligence, machine learning, and/or the like. Continuing with the previous example, the recommendation platform may process millions, billions, trillions, etc. of data elements when processing the data received from the external information sources. In some cases, processing the data may include use of a big data analysis tool and/or technique.

As shown by reference number 140, the recommendation platform may analyze the data using an organization operating model. For example, the recommendation platform may map data to portions of the organization operating model to identify a manner in which the organization implements a process and/or operates. Additionally, or alternatively, and as another example, the recommendation platform may use the organization operating model to perform a comparison of the data and a threshold, such as to identify a deficiency of the organization relative to a benchmark or industry standard. In some implementations, the recommendation platform may analyze the data to identify a deficiency related to the performance of the process and/or operations of the organization.

An example of an organization operating model is shown by reference number 150. The organization operating model may represent a structure or organization of another healthcare organization (e.g., identified as a high-performing healthcare organization), a benchmark healthcare organization, a threshold, an industry standard, and/or the like. In some implementations, the organization operating model may identify functional areas of the organization (e.g., shown as A1, A2, etc.). For example, a functional area may relate to channels of the organization (e.g., web, mobile, mail, etc.), customer data analytics (e.g., customer profile and preferences, interaction management, etc.), customer relationship management (e.g., marketing, service, etc.), and/or the like.

In some implementations, the organization operating model may identify sub-areas corresponding to a functional area (e.g., shown as S1 and S2 as sub-areas of functional area A1, and S3 and S4 as sub-areas of functional area A2). For example, sub-areas corresponding to channels of the organization may include web, mobile, mail, text, social media, and/or the like.

Figure 1C:
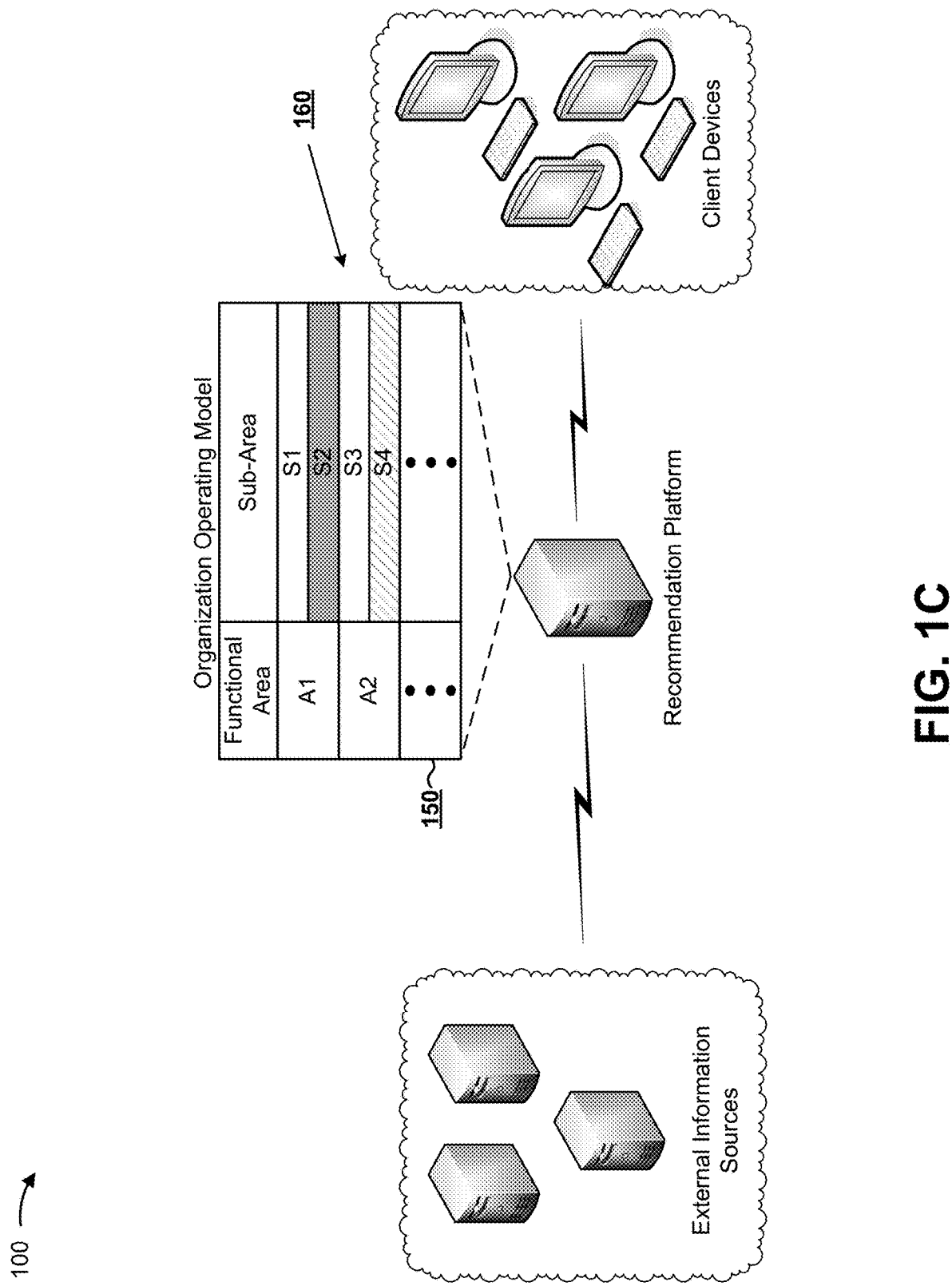

As shown in FIG. 1C, and by reference number 160, the recommendation platform may identify a deficiency related to performance of a process and/or operations of the organization and/or may identify a manner in which the organization can be improved. In some implementations, the recommendation platform may identify sub-areas without a deficiency (e.g., that satisfy a threshold or that do not satisfy a threshold that indicates a deficiency), as shown as white boxes (e.g., S1 and S3). In some implementations, the recommendation platform may identify sub-areas that have a deficiency (e.g., that satisfy a first threshold indicating a deficiency but not a second threshold indicating a more or less severe deficiency), as shown as a striped box (e.g., S4).

In some implementations, the recommendation platform may identify sub-areas that have a different deficiency (e.g., that satisfy a first threshold and a second threshold indicating a deficiency), as shown as a dark shaded box (e.g., S2). The recommendation platform may identify the deficiency using thresholds, information identifying an industry standard, and/or the like. In this way, the recommendation platform may identify a deficiency related to performance of a process and/or operations of an organization and/or identify a manner in which to improve the performance of the process and/or operations.

Figure 1D:
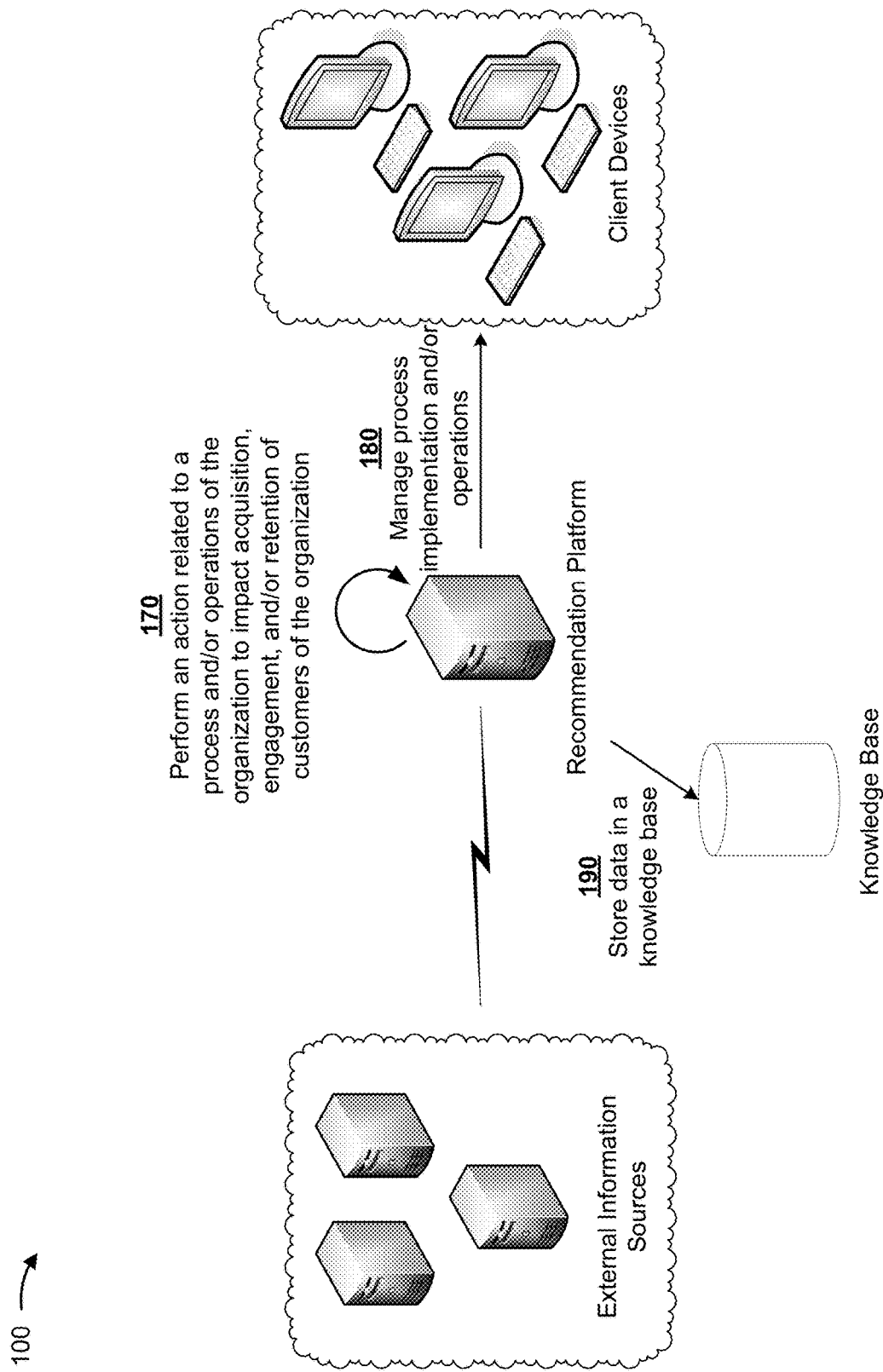

As shown in FIG. 1D, and by reference number 170, the recommendation platform may perform an action related to a process and/or operations of the organization, such as to impact acquisition, engagement, and/or retention of customers of the organization. For example, the recommendation platform may perform an action to positively impact a deficiency related to a performance of the process and/or operations of the organization. For example, the recommendation platform may perform an action to reduce or eliminate a deficiency, to increase an efficiency of a process and/or operations of the organization (e.g., thereby conserving processing resources of devices that the organization uses to implement the process and/or operations), and/or the like.

As shown by reference number 180, the recommendation platform may manage implementation of a process and/or operations of the organization. For example, the recommendation platform may provide a set of instructions to one or more client devices to perform a process in a particular manner. Additionally, or alternatively, and as another example, the recommendation platform may gather data, relating to metrics, from the client devices and may adjust performance of the process and/or operations of the organization based on the metrics. Continuing with the previous example, the recommendation platform may dynamically adjust the performance of the process and/or operations (e.g., in real-time or near real-time as the recommendation platform receives data).

As shown by reference number 190, the recommendation platform may store the data associated with the analysis in a knowledge base (e.g., a knowledge graph). Additionally, or alternatively, the recommendation platform may store data gathered during management of the process and/or operations of the organization. In some implementations, the knowledge base may include data from other analyses. For example, the recommendation platform may use the knowledge base to perform machine learning, data analysis, etc., to improve analysis of the process and/or operations.

In this way, implementations described herein increase an efficiency of analyzing a process of an organization and/or operations of the organization. In addition, the implementations improve an accuracy of a result and/or output of a process (e.g., by reducing a related deficiency), thereby conserving processing resources that would otherwise be consumed due to inaccurate results and/or outputs. Further, the implementations improve performance of a process and/or operations of an organization, thereby conserving processing resources and/or computing resources of devices used to implement the process and/or the operations.

Implementations described herein equally apply to various kinds of organizations, such as organizations relating to healthcare, manufacturing, construction, information technology, and/or the like.

As indicated above, FIGS. 1A-1D are provided merely as an example. Other examples are possible and may differ from what was described with regard to FIGS. 1A-1D.

Figure 2:
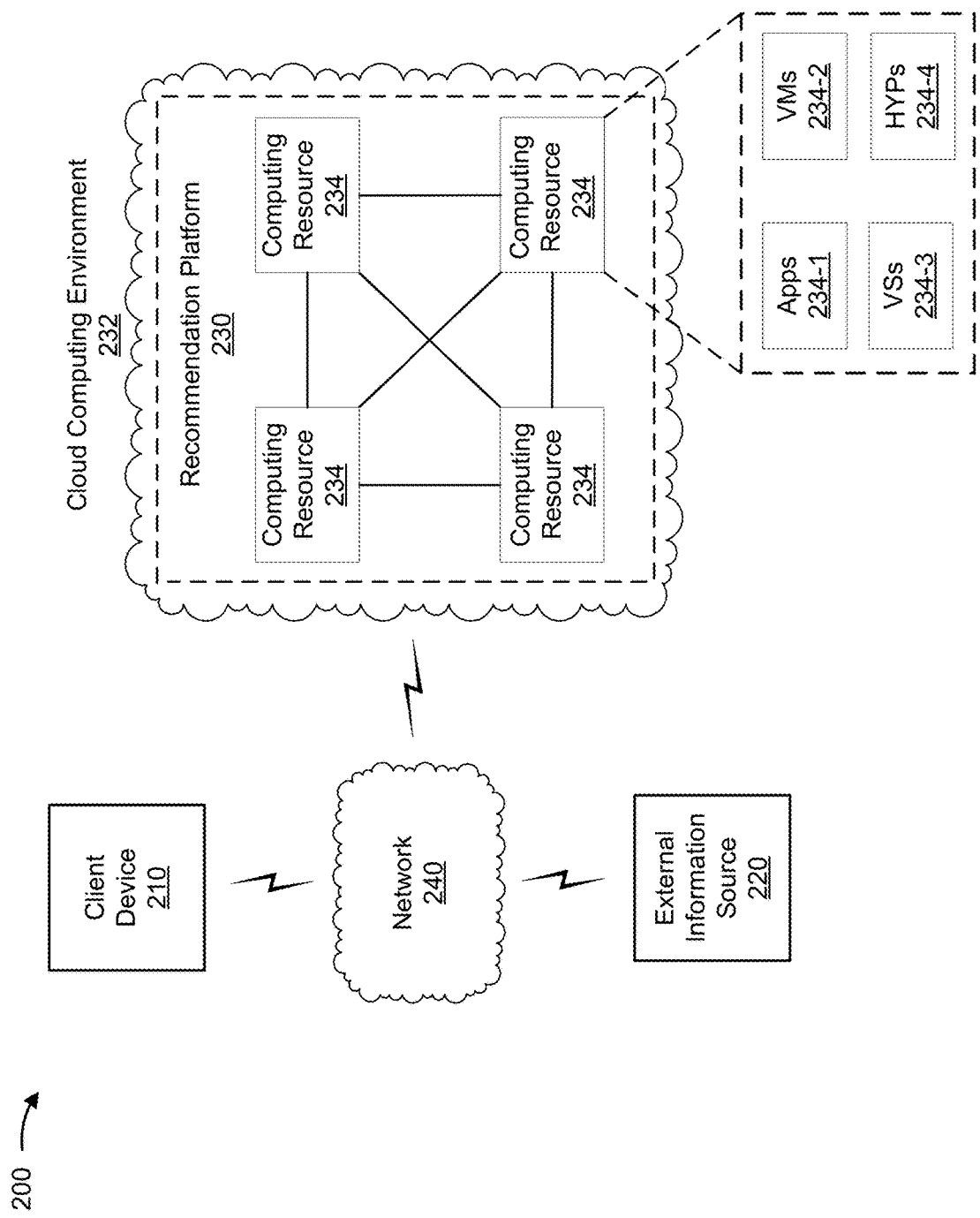
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include client device 210, external information source 220, recommendation platform 230, cloud computing environment 232, and a set of computing resources 234. Devices of environment 200 may interconnect via wired connections, wireless connections, or a combination of wired and wireless connections.

Client device 210 includes one or more devices capable of receiving, generating, storing, processing, and/or providing information associated with analyzing data related to customers of an organization. For example, client device 210 may include a desktop computer, a mobile phone (e.g., a smart phone or a radiotelephone), a laptop computer, a tablet computer, a gaming device, a wearable communication device (e.g., a smart wristwatch or a pair of smart eyeglasses), or a similar type of device. In some implementations, client device 210 may receive data associated with an analysis that recommendation platform 230 has performed, as described elsewhere herein. Additionally, or alternatively, client device 210 may provide information for display (e.g., information related to an analysis of data related to customers of an organization), as described elsewhere herein.

External information source 220 includes one or more devices capable of receiving, generating, storing, processing, and/or providing information associated with an analysis of customers of an organization. For example, external information source 220 may include a server (e.g., in a data center or a cloud computing environment), a data center (e.g., a multi-server micro data center), a workstation computer, a virtual machine (VM) provided in a cloud computing environment, or a similar type of device. In some implementations, external information source 220 may provide, to recommendation platform 230, information related to customers of an organization, as described elsewhere herein. Additionally, or alternatively, external information source 220 may store information related to an analysis of customers of an organization, as described elsewhere herein.

Recommendation platform 230 includes one or more devices capable of analyzing data related to customers of an organization. For example, recommendation platform 230 may include a cloud server or a group of cloud servers. In some implementations, recommendation platform 230 may be designed to be modular such that certain software components can be swapped in or out depending on a particular need. As such, recommendation platform 230 may be easily and/or quickly reconfigured for different uses.

In some implementations, as shown, recommendation platform 230 may be hosted in cloud computing environment 232. Notably, while implementations described herein describe recommendation platform 230 as being hosted in cloud computing environment 232, in some implementations, recommendation platform 230 may not be cloud-based (i.e., may be implemented outside of a cloud computing environment) or may be partially cloud-based.

Cloud computing environment 232 includes an environment that hosts recommendation platform 230. Cloud computing environment 232 may provide computation, software, data access, storage, and/or other services that do not require end-user knowledge of a physical location and configuration of a system and/or a device that hosts recommendation platform 230. As shown, cloud computing environment 232 may include a group of computing resources 234 (referred to collectively as "computing resources 234" and individually as "computing resource 234").

Computing resource 234 includes one or more personal computers, workstation computers, server devices, or another type of computation and/or communication device. In some implementations, computing resource 234 may host recommendation platform 230. The cloud resources may include compute instances executing in computing resource 234, storage devices provided in computing resource 234, data transfer devices provided by computing resource 234, etc. In some implementations, computing resource 234 may communicate with other computing resources 234 via wired connections, wireless connections, or a combination of wired and wireless connections.

As further shown in FIG. 2, computing resource 234 may include a group of cloud resources, such as one or more applications ("APPs") 234-1, one or more virtual machines ("VMs") 234-2, one or more virtualized storages ("VSs") 234-3, or one or more hypervisors ("HYPs") 234-4.

Application 234-1 includes one or more software applications that may be provided to or accessed by one or more devices of environment 200. Application 234-1 may eliminate a need to install and execute the software applications on devices of environment 200. For example, application 234-1 may include software associated with recommendation platform 230 and/or any other software capable of being provided via cloud computing environment 232. In some implementations, one application 234-1 may send/receive information to/from one or more other applications 234-1, via virtual machine 234-2.

Virtual machine 234-2 includes a software implementation of a machine (e.g., a computer) that executes programs like a physical machine. Virtual machine 234-2 may be either a system virtual machine or a process virtual machine, depending upon use and degree of correspondence to any real machine by virtual machine 234-2. A system virtual machine may provide a complete system platform that supports execution of a complete operating system ("OS"). A process virtual machine may execute a single program, and may support a single process. In some implementations, virtual machine 234-2 may execute on behalf of a user (e.g., a user of client device 210), and may manage infrastructure of cloud computing environment 232, such as data management, synchronization, or long-duration data transfers.

Virtualized storage 234-3 includes one or more storage systems and/or one or more devices that use virtualization techniques within the storage systems or devices of computing resource 234. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 234-4 provides hardware virtualization techniques that allow multiple operating systems (e.g., "guest operating systems") to execute concurrently on a host computer, such as computing resource 234. Hypervisor 234-4 may present a virtual operating platform to the guest operating systems, and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, or another type of cellular network), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
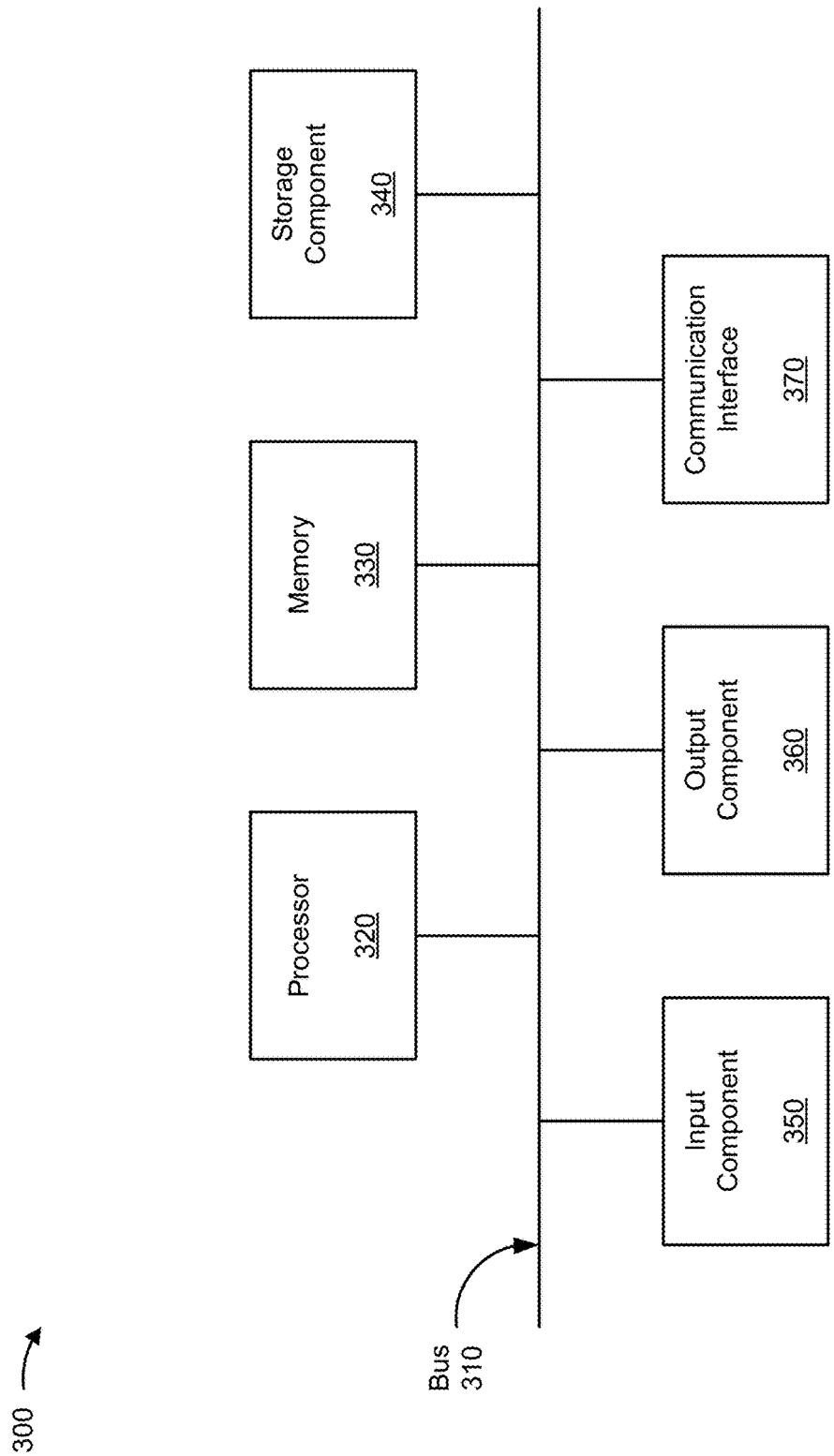
FIG. 3 is a diagram of example components of one or more devices of FIG. 2.

FIG. 3 is a diagram of example components of a device 300. Device 300 may correspond to client device 210, external information source 220, and/or recommendation platform 230. In some implementations, client device 210, external information source 220, and/or recommendation platform 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operations and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for automatic analysis of process and/or operations data for channel optimization. In some implementations, one or more process blocks of FIG. 4 may be performed by recommendation platform 230. In some implementations, one or more process blocks of FIG. 4 may be performed by another device or a group of devices separate from or including recommendation platform 230, such as client device 210 and external information source 220.

As shown in FIG. 4, process 400 may include receiving data associated with customers, a customer-related process, and/or customer-related operations of an organization (block 410). For example, recommendation platform 230 may receive data associated with customers, a customer-related process, and/or customer-related operations of an organization. In some implementations, recommendation platform 230 may receive the data periodically, according to a schedule, based on input from a user of client device 210, based on requesting the data, and/or the like. In some implementations, recommendation platform 230 may receive the data from external information source 220.

In some implementations, the data may relate to customers, a customer-related process, and/or customer-related operations of an organization. For example, the data may relate to channels via which a customer interacts with the organization (e.g., an on-line channel, a telephone channel, or a mail channel). Additionally, or alternatively, and as another example, the data may relate to a demographic of customers of the organization (e.g., a nationality, an ethnicity, a gender, an age, a financial status, etc. of the customers).

In some implementations, the data may relate to a performance of a process of the organization and/or operations of the organization. In some implementations, the data may relate to a value received and/or expended by the organization (e.g., related to acquiring, engaging, or retaining a customer). Additionally, or alternatively, the data may relate to a manner in which the organization has implemented the process. For example, the data may include data elements that identify a quantity of people associated with performance of a process, departments and/or functional areas of the organization related to the process, computing/processing/memory resources associated with implementation of the process, and/or the like.

Additionally, or alternatively, the data may relate to a manner in which a customer interacts with the organization. For example, the data may relate to, or identify, the systems with which the customer interacts when interacting with the organization, such as a quantity and/or type of systems with which the customer interacts, processing and/or computing resources that the systems consume during a customer interaction, and/or the like. Additionally, or alternatively, and as another example, the data may relate to channels via which a customer obtains goods and/or services from the organization (e.g., retail or on-line), a manner in which error tickets generated during a customer interaction are handled, and/or the like.

Additionally, or alternatively, the data may relate to metrics associated with the process and/or the operations of the organization related to customers. For example, the metrics may include a quantity of customers serviced by the organization, quantity and/or types of services provided to a customer, purchase information related to a customer, errors related to processing customer information, an amount of time, processing resources, and/or computing resources used to implement a process and/or perform operations of the organization, and/or the like.

Additionally, or alternatively, and as another example, the data may relate to customer relationship management of the organization (e.g., a manner in which the organization interacts with a customer). Additionally, or alternatively, and as another example, the data may relate to a marketing process and/or operations of the organization, such as data that identifies marketing channels of the organization, values associated with a marketing process and/or operations, customers acquired based on a marketing process and/or operations, and/or the like. Additionally, or alternatively, and as another example, the data may relate to an experience of the customer (e.g., an amount of time a customer spends acquiring a good and/or service from the organization, whether the organization has received a complaint from a customer regarding a good and/or service, etc.).

In some implementations, the data may include cross-industry and/or multi-domain data. For example, the data may include data related to various types of organizations, organizations in various industries, and/or the like. In this way, recommendation platform 230 may receive data related to different types of organization in different industries (e.g., for analysis), thereby improving an analysis of an organization.

In some implementations, the data may include text (e.g., text from customer data records, registration forms, organization charts, consumer surveys, etc.), audio data, and/or video data. In some implementations, recommendation platform 230 may receive the data in a file. For example, recommendation platform 230 may receive the data in a comma separated values (CSV) file, a spreadsheet file, a text file, and/or the like. In this way, recommendation platform 230 may receive various types of files. In some implementations, recommendation platform 230 may receive millions, billions, or trillions of data elements when receiving the data.

In some implementations, recommendation platform 230 may store the data. For example, recommendation platform 230 may store the data using memory resources associated with recommendation platform 230. In some implementations, when storing the data, recommendation platform 230 may aggregate and/or merge the data with other data, deduplicate the data, and/or identify missing or corrupted data and obtain replacement data (e.g., using information related to the data, querying data from external information source 220, cross-referencing the data to identify the missing/corrupted data, and/or the like). This conserves memory resources of recommendation platform 230 and/or conserves processing resources of recommendation platform 230 by reducing errors in the data, reducing duplicate data, and/or the like. In some implementations, recommendation platform 230 may use a big data tool to aggregate and/or merge the data (e.g., to aggregate and/or merge millions, billions, trillions, etc., of data elements). In this way, recommendation platform 230 may receive a data set that cannot be received and/or processed manually, thereby increasing an efficiency of receiving data related to an organization.

In this way, recommendation platform 230 may receive data associated with a performance of a process and/or operations of an organization.

As further shown in FIG. 4, process 400 may include processing the data using a technique based on receiving the data (block 420). For example, recommendation platform 230 may process the data using a technique. In some implementations, recommendation platform 230 may process millions, billions, trillions, etc. of data elements when processing the data. In this way, recommendation platform 230 may process a data set that cannot be processed manually.

In some implementations, the technique may include natural language processing, text analysis, computational linguistics, and/or or the like. In some implementations, when processing the data using natural language processing, recommendation platform 230 may process the data to identify a term included in the data. For example, recommendation platform 230 may adjust characters (e.g., add characters, remove characters, etc.), adjust spacing in the data (e.g., add or remove spaces), expand acronyms included in the data (e.g., replace "EPA" with "Environmental Protection Agency"), replace a symbol with a term (e.g., replace an "@" symbol with the term "at"), convert a term included in the data to a root term (e.g., convert "processing," "processed," or "processor" to "process"), and/or the like.

Additionally, or alternatively, the technique may include pattern recognition, trend analysis, and/or the like. For example, recommendation platform 230 may use a big data tool to process millions, billions, and/or trillions of data elements to identify previously unidentifiable relationships and/or trends among data elements of the data, such as to identify a deficiency related to the data, to identify a manner in which to positively impact a deficiency, and/or the like.

Additionally, or alternatively, the technique may include automatic speech recognition (ASR), computer speech recognition, speech-to-text, and/or the like. For example, recommendation platform 230 may convert audio from an interview or customer support call to text. In some implementations, recommendation platform 230 may process a file associated with the data. In some implementations, recommendation platform 230 may process multiple file types. This improves performance of recommendation platform 230 by permitting recommendation platform 230 to process files of various types (e.g., relative to processing a single type of file).

In some implementations, recommendation platform 230 may process the data to identify metadata associated with the data (e.g., an identifier associated with the data that identifies a process with which the data is associated, a timestamp associated with the data, etc.). For example, recommendation platform 230 may process the data to identify a process with which the data is associated, a functional area of the organization with which the data is associated, operations of the organization with which the data is associated, and/or the like. This permits recommendation platform 230 to quickly and efficiently identify metadata associated with the data, thereby conserving processing resources of recommendation platform 230.

In some implementations, recommendation platform 230 may process the data to permit analysis of the data. For example, by processing the data, recommendation platform 230 may reduce errors associated with the data, may format the data such that recommendation platform 230 can map the data to an operating model (as described below), may normalize the data to permit inter-organization comparisons, and/or the like. This conserves processing resources of recommendation platform 230 and improves analyses using the data relative to using unprocessed data.

In this way, recommendation platform 230 may process the data using a technique based on receiving the data.

As further shown in FIG. 4, process 400 may include mapping the data to an organization operating model based on processing the data (block 430). For example, recommendation platform 230 may map the data to an organization operating model based on processing the data. In some implementations, the organization operating model may include a model that identifies an area of an organization (e.g., a functional area and/or a sub-area of a functional area that the organization uses to implement a process and/or operations).

In some implementations, the organization operating model may be based on analyses of other organizations. For example, the organization operating model may represent a benchmark structure and/or organizational structure of another healthcare organization (e.g., an organization identified as a high-performing healthcare organization), an industry standard, and/or the like. In some implementations, recommendation platform 230 may use the operating model to identify a rule (e.g., related to data, a functional area, or a sub-area), a threshold related to data, an industry standard, a metric related to a process and/or operations of an organization, and/or the like to apply to data related to a process and/or operations of an organization when analyzing the data. This permits recommendation platform 230 to quickly identify a rule, a threshold, a metric, and/or the like by mapping data to an organization operating model.

In some implementations, the organization operating model may be based on a type of healthcare organization being analyzed. For example, recommendation platform 230 may use an organization operating model for an organization, a retail operating model for a retail organization, and/or the like. Additionally, or alternatively, the organization operating model may be based on a type of analysis being performed. For example, the organization operating model may include functional areas and/or sub-areas specific to analyzing customer acquisition when analyzing operations of the organization related to customer acquisition, functional areas and/or sub-areas specific to analyzing customer engagement when analyzing operations of the organization related to customer engagement, and/or the like.

In some implementations, recommendation platform 230 may map the data to an area and/or a sub-area of the organization operating model. In some implementations, recommendation platform 230 may map the data based on an identifier associated with the data (e.g., an identifier that identifies a functional area and/or a sub-area with which the data is associated). This conserves processing resources of recommendation platform 230 via quick and efficient mapping of the data.

Additionally, or alternatively, recommendation platform 230 may map the data based on a type of the data (e.g., when the functional areas of the organization do not match the functional areas of the organization operating model). For example, recommendation platform 230 may map the data based on previous mappings, using artificial intelligence, and/or the like. This improves mapping of the data by permitting recommendation platform 230 to map data when functional areas of the organization being analyzed do not match functional areas of the organization operating model (e.g., relative to a device that cannot map data when functional areas or sub-areas of an organization do not match functional areas or sub-areas of an organization operating model).

In some implementations, recommendation platform 230 may map the data to permit analysis of the data. For example, recommendation platform 230 may map the data to permit a comparison of a process implemented by the organization and another healthcare organization identified as a high performing healthcare organization, to identify a deficiency related to a process and/or operations of the organization, and/or the like, as described in more detail elsewhere herein.

In some implementations, recommendation platform 230 may generate the organization operating model prior to mapping the data. For example, recommendation platform 230 may receive data associated with other healthcare organizations (e.g., different from the organization that recommendation platform 230 is analyzing) and may generate the organization operating model based on the received data. Continuing with the previous example, recommendation platform 230 may generate an organization operating model that identifies functional areas, or sub-areas, of the other healthcare organizations based on the received data (e.g., data that identifies functional areas and/or sub-areas of the other healthcare organizations, a manner in which the other healthcare organizations implement a process and/or operations, etc.). In this way, recommendation platform 230 may generate an organization operating model.

In this way, recommendation platform 230 may map the data to an organization operating model based on processing the data.

As further shown in FIG. 4, process 400 may include performing an analysis of the data based on mapping the data to the organization operating model (block 440). For example, recommendation platform 230 may perform an analysis of the data based on mapping the data to the organization operating model. In some implementations, recommendation platform 230 may use a metric, a rule, data related to a process and/or operations of another healthcare organization (e.g., a high performing healthcare organization), and/or the like identified by an organization operating model to perform the analysis. For example, when recommendation platform 230 maps data to the organization operating model, recommendation platform 230 may identify a metric, a rule, other data, and/or the like associated with a functional area and/or a sub-area of the operating model to which the data was mapped. Continuing with the previous example, recommendation platform 230 may use the identified metric, rule, data, and/or the like to perform the analysis.

In some implementations, recommendation platform 230 may perform the analysis to identify a deficiency related to a process implemented by an organization and/or a manner in which to improve operations of the organization. In some implementations, recommendation platform 230 may identify a deficiency when a metric does not satisfy a threshold, satisfies a first threshold rather than a second threshold, fails to satisfy a threshold by a threshold amount, and/or the like. Additionally, or alternatively, recommendation platform 230 may compare functional areas of an organization and an organization operating model and may identify a deficiency when the organization is missing a functional area or a sub-area included in the organization operating model (e.g., the functional areas of the organization and the organization operating model do not match). Additionally, or alternatively, recommendation platform 230 may identify a deficiency related to volume, storage capacity, installed software, and/or processing capabilities of computer hardware and/or electronic devices utilized in performing a process and/or operations of the organization.

In some implementations, recommendation platform 230 may identify a deficiency and/or a manner in which to improve an organization by comparing functional areas of the organization that are used to implement a process and functional areas of another healthcare organization (e.g., by using the organization operating model), and may determine that the functional areas used are different. In this case, recommendation platform 230 may identify a deficiency and/or a manner in which to improve the operations of an organization by identifying functional areas that the organization can use to implement a process and that are different than the functional areas that the organization is using.

Additionally, or alternatively, recommendation platform 230 may identify a deficiency and/or a manner in which to improve an organization by identifying a potentially inefficient combination of functional areas or sub-areas used to implement a process. For example, recommendation platform 230 may identify the potentially inefficient combination of functional areas or sub-areas based on previous analyses that identified an inefficient combination of functional areas, using machine learning, using pattern recognition, and/or the like. In this case, recommendation platform 230 may identify a deficiency and/or a manner in which to improve operations of the organization by identifying a more efficient combination of functional areas and/or sub-areas to use to implement a process and/or operations, thereby conserving processing resources related to implementing the process and/or operations.

Additionally, or alternatively, recommendation platform 230 may identify a deficiency and/or a manner in which to improve an organization by identifying a threshold quantity of functional areas or sub-areas that the organization uses to implement the process and/or operations. For example, the threshold quantity may indicate a complex implementation of a process and/or operations, thereby reducing efficiency of the operations of the organization. In this way, recommendation platform 230 may identify a deficiency and/or a manner in which to improve a process and/or operations of the organization by identifying a more efficient combination of functional areas and/or sub-areas to use to implement a process and/or operations.

Additionally, or alternatively, recommendation platform 230 may identify a deficiency and/or a manner in which to improve the organization by determining that volume, storage capacity, installed software, and/or processing capabilities of computer hardware and/or electronic devices utilized in performing a process and/or operations of the organization do not satisfy a threshold, satisfy a threshold, satisfy a first threshold but not a second threshold, and/or the like. This conserves processing resources related to implementation of a process and/or operations, improves an efficiency of a process and/or operations, and/or the like.

In some implementations, recommendation platform 230 may generate a score related to an identified deficiency. For example, the score may relate to a severity of an inefficiency, resources and/or expenses associated with fixing an identified deficiency or with improving operations, a priority of the deficiency (e.g., for fixing the deficiency), a priority of improving the operations, and/or the like. In this way, recommendation platform 230 may quickly and efficiently prioritize deficiencies and determine a severity of a first deficiency relative to a second deficiency.

In some implementations, when performing the analysis, recommendation platform 230 may identify a current customer-channel combination of the organization. For example, recommendation platform 230 may determine a percentage of customers that purchase goods and/or services via various channels of the organization, the types of customers acquired, engaged, and/or retained via various channels of the organization, and/or the like. In some implementations, recommendation platform 230 may determine a value associated with each of the channels. For example, recommendation platform 230 may determine a value received via each of the various channels, a value expended for each of the various channels, a quantity of employee hours spent maintaining each of channels or serving customers of each of the channels, and/or the like.

In some implementations, recommendation platform 230 may receive information that identifies a customer-channel combination of another organization. For example, the other organization may be in the same or a different industry as the organization that recommendation platform 230 is analyzing. In some implementations, recommendation platform 230 may perform an analysis of the information to identify a trend related to a customer-channel combination (e.g., to identify a manner in which customer-channel combinations are changing). For example, recommendation platform 230 may perform the analysis to identify a trend related to channel preferences of customers (e.g., to determine a trend of customers using an on-line channel rather than a retail channel, a not-yet-implemented (e.g., future) customer-channel combination of the organization being analyzed, etc.). Additionally, or alternatively, recommendation platform 230 may determine a value of the other customer-channel combinations to determine a future value of a customer-channel combination of the organization being analyzed and/or may perform an action to positively impact the future value of the customer-channel combination.

In some implementations, recommendation platform 230 may generate an objective related to a customer-channel combination for the organization based on the customer-channel combinations for the other organizations. For example, recommendation platform 230 may determine that other organizations acquire at least 10 percent of customers via an on-line channel. Continuing with the previous example, recommendation platform 230 may generate an objective for the organization to acquire at least 10 percent of customers via an on-line channel. Additionally, or alternatively, recommendation platform 230 may receive information identifying an objective (e.g., from client device 210).

In some implementations, when recommendation platform 230 receives information identifying an objective, recommendation platform 230 may perform an analysis of the objective (e.g., perform an action based on generating the objective). For example, recommendation platform 230 may perform an analysis to determine whether the organization can satisfy the objective, a manner in which the organization can satisfy the objective, a value of satisfying the objective (e.g., a value that the organization needs to expend to implement a new channel, to obtain additional hardware and/or software to satisfy the objective, a value that the organization saves by satisfying the objective, etc.), and/or the like. In some implementations, recommendation platform 230 may determine whether a value associated with an objective satisfies a threshold, and may perform an action (described in more detail below) based on determining whether the value satisfies the threshold.

In some implementations, recommendation platform 230 may use data associated with other organizations to perform the analysis of the objective. For example, assume that the objective is to increase a percentage of customers acquired via an on-line channel. Further assume, for example, that recommendation platform 230 determines that no other organization for which recommendation platform 230 has data acquires more than eight percent of customers via an on-line channel. In this case, recommendation platform 230 may determine that the objective may be difficult to satisfy, or cannot be satisfied, and/or that satisfying the object may require recommendation platform 230 to expend a threshold value.

In some implementations, recommendation platform 230 may store a result of the analysis in a knowledge base or knowledge graph. For example, recommendation platform 230 may aggregate the data with information for results of other analyses. In some implementations, recommendation platform 230 may use the knowledge base to perform machine learning to improve future analyses of the same or a different healthcare organization, to perform a big data analysis, and/or the like. In some implementations, a knowledge base or knowledge graph may include technology used to store complex structured and unstructured data used by a computer system.

In this way, recommendation platform 230 may perform an analysis of the data based on mapping the data to an organization operating model.

As further shown in FIG. 4, process 400 may include performing, by the recommendation platform, an action to positively impact the performance of the organization based on performing the analysis (block 450). For example, recommendation platform 230 may perform an action to positively impact the performance of the process and/or the operations of the organization based on performing the analysis. In some implementations, a positive impact may occur when an action causes a desired result or action to be achieved. Additionally, or alternatively, a positive impact may occur when an action increases the likelihood that a desired result of an action will be achieved.

In some implementations, recommendation platform 230 may generate a recommendation. For example, recommendation platform 230 may generate a recommendation to use different functional areas to implement a process and/or operations, a recommendation to use different systems to implement a process and/or operations (e.g., to consolidate systems), a recommendation to use different sub-areas to implement a process and/or operations, a recommendation to add a process and/or operations associated with a functional area or sub-area, a recommendation to remove a process and/or operations associated with a functional area or sub-area, and/or the like.

In some implementations, recommendation platform 230 may generate the recommendation using information related to the analysis. For example, recommendation platform 230 may generate a recommendation to fix a particular deficiency identified during an analysis. In some implementations, recommendation platform 230 may generate multiple recommendations.

In some implementations, recommendation platform 230 may generate a score for each of the multiple recommendations. For example, recommendation platform 230 may generate a score based on a predicted impact of the recommendation (e.g., as determined using data from prior analyses and prior implemented recommendations).

In some implementations, recommendation platform 230 may provide information identifying a recommendation to a device to cause the device to implement the recommendation based on a score for the recommendation. For example, recommendation platform 230 may provide information identifying a recommendation that has the highest score relative to other scores for other recommendations, that has a threshold score, and/or the like. In this way, recommendation platform 230 may optimize providing recommendations to a device that implements a process and/or operations of an organization, thereby increasing an efficiency of providing recommendations and/or conserving processing resources of recommendation platform 230 (e.g., relative to providing all recommendations, providing a recommendation that may fail to have a predicted result, etc.).

In some implementations, recommendation platform 230 may send a message (e.g., an email or a short message service (SMS) message) to client device 210. For example, the message may include information related to the analysis and/or a generated recommendation. In some implementations, recommendation platform 230 may schedule a meeting (e.g., to discuss the analysis or a generated recommendation). For example, recommendation platform 230 may schedule a meeting using electronic calendars of individuals associated with the organization to identify an available time for the meeting.

In some implementations, recommendation platform 230 may send a set of instructions to modify a manner in which devices implement a process and/or operations. For example, recommendation platform 230 may send a set of instructions to modify which systems and/or devices are used to implement a process (e.g., to reduce or increase a quantity of systems used). In this way, recommendation platform 230 may modify a manner in which a system and/or device implements a process and/or operations.

In some implementations, recommendation platform 230 may manage implementation of a process and/or operations. For example, recommendation platform 230 may track metrics associated with implementation of a process and/or operations, may perform an analysis (e.g., of the metrics) to determine a more efficient manner of performing the process and/or operations, and/or the like. In this case, recommendation platform 230 may send a set of instructions (e.g., to client device 210) when recommendation platform 230 identifies a more efficient manner for implementing the process and/or operations.

In some implementations, recommendation platform 230 may provide information for an analysis to another recommendation platform 230. For example, recommendation platform 230 may provide the information to improve future analyses of the other recommendation platform 230. This improves an accuracy of an analysis of the other recommendation platform 230, thereby conserving processing resources that would otherwise be consumed due to an inaccurate or inefficient analysis.

In some implementations, recommendation platform 230 may monitor post-recommendation actions, such as to determine whether an impact of an action matches a predicted impact. For example, if recommendation platform 230 generates a recommendation to reduce a quantity of devices used to implement a process, recommendation platform 230 may monitor the process to determine whether the devices that are implementing the process use fewer processing resources after the quantity of devices is reduced. This improves implementation of a recommendation by preventing a device from implementing an ineffective recommendation.

In some implementations, recommendation platform 230 may bring a device and/or software online or offline. For example, recommendation platform 230 may send a set of instructions to a device, install and/or activate software on a device, and/or the like. Additionally, or alternatively, recommendation platform 230 may update software installed on a device. Additionally, or alternatively, recommendation platform 230 may push software to a device, so as to update the software. In this way, recommendation platform 230 may improve functioning of a device via updating of software, adjusting whether the device is online or offline, and/or the like.

In some implementations, recommendation platform 230 may perform the actions described herein in real-time or near real-time. For example, recommendation platform 230 may analyze and modify a process and/or operations of an organization as the organization is implementing the process and/or the operations. This conserves processing resources of a device used to implement the process and/or operations by reducing an amount of time that the device implements a process and/or operations that include a deficiency (e.g., relative to delayed performance of an action).

In this way, recommendation platform 230 may perform an action to positively impact a performance of a process and/or operations of an organization based on performing an analysis.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
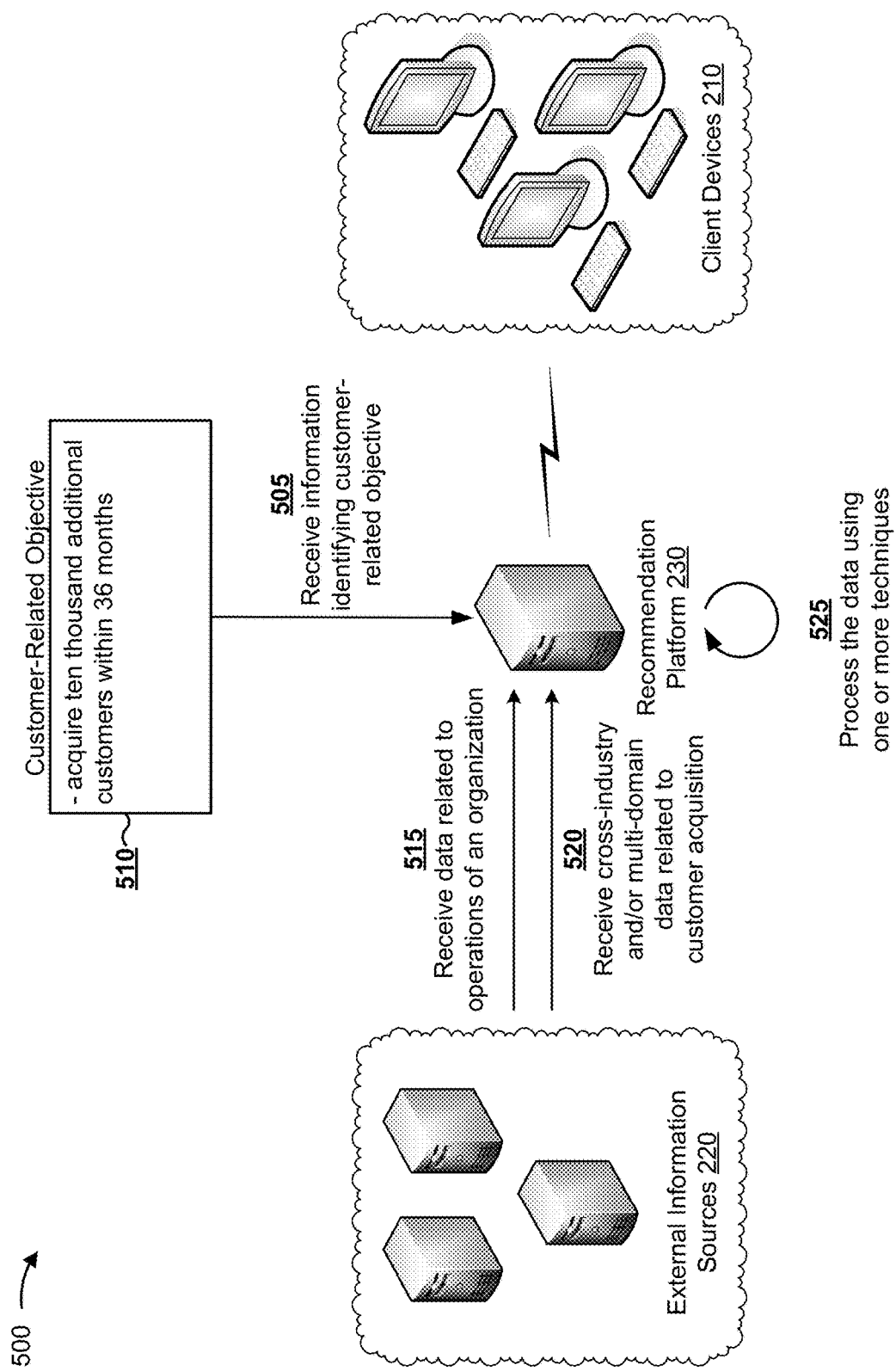
FIGS. 5A-5C are diagrams of an example implementation relating to the example process shown in FIG. 4.
Figure 5B:
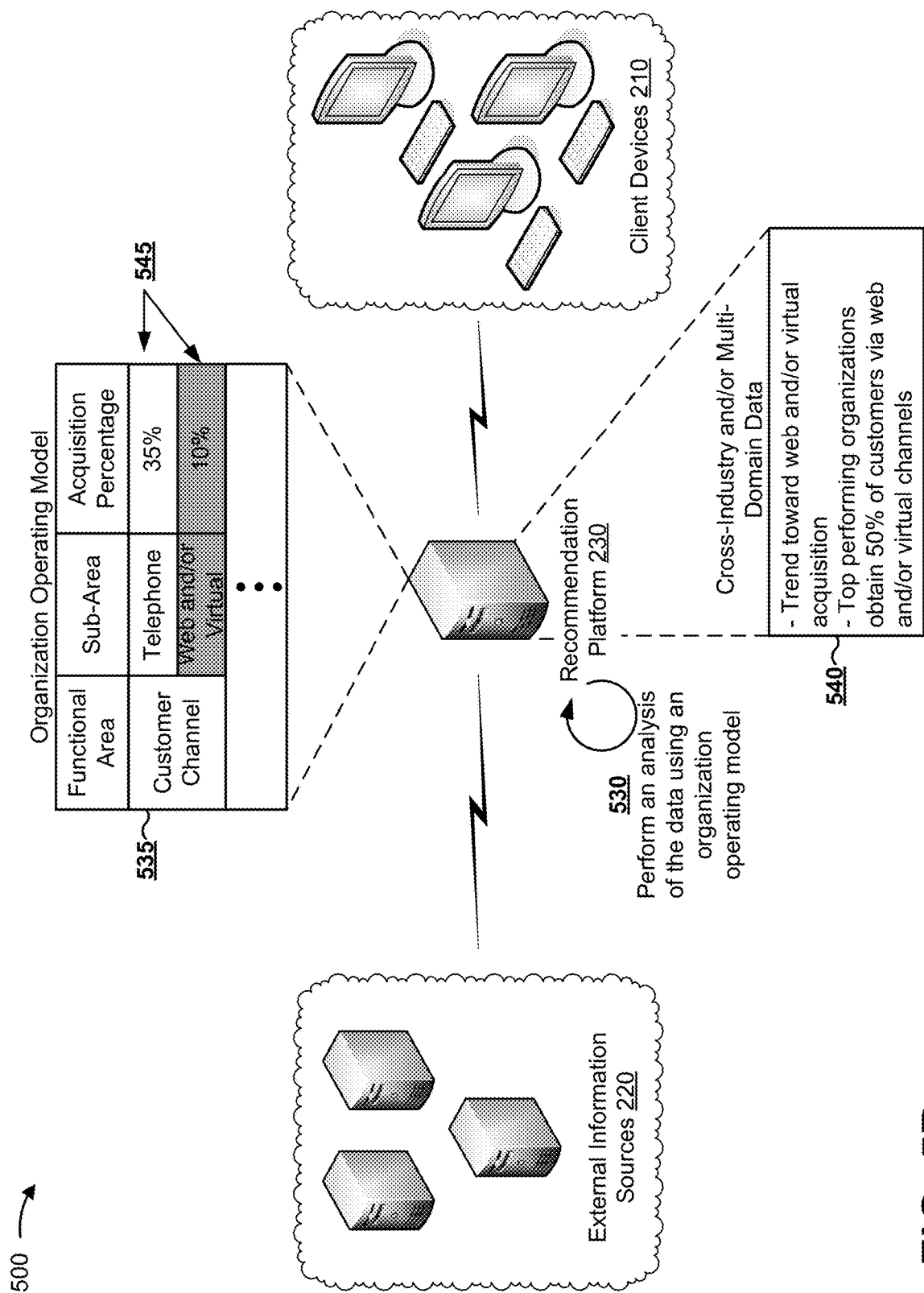
Figure 5C:
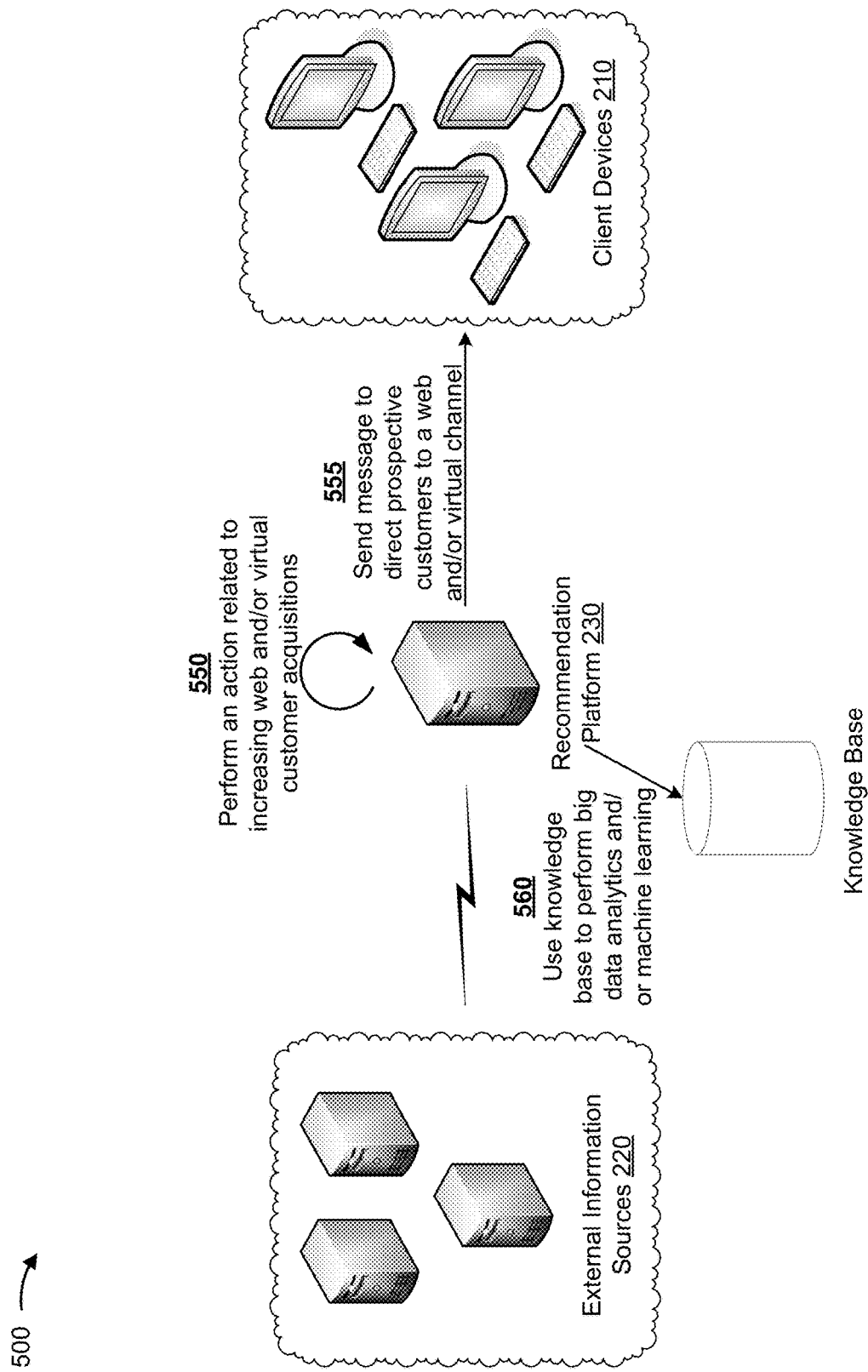

FIGS. 5A-5C are diagrams of an example implementation 500 relating to example process 400 shown in FIG. 4. FIGS. 5A-5C show an example of automatic analysis of process and/or operations data for channel optimization. As shown in FIGS. 5A-5C, example implementation 500 may include client devices 210, external information sources 220, and recommendation platform 230.

As shown in FIG. 5A, and by reference number 505, recommendation platform 230 may receive information identifying a customer-related objective (e.g., an objective related to acquiring, engaging, or retaining customers) for an organization, such as a payer organization that pays for healthcare services on behalf of a customer or a provider organization that provides healthcare services to the customer. For example, a customer-related objective may relate to customer acquisition, customer engagement, customer retention, and/or the like. As shown by reference number 510, an example of a customer-related objective for an organization may include acquiring ten thousand additional customers within 36 months.

As shown by reference number 515, recommendation platform 230 may receive data related to operations of an organization. For example, recommendation platform 230 may receive information that identifies channels via which the organization acquires new customers, marketing operations that the organization performs to acquire additional customers, processes that the organization performs to sign up additional customers, and/or the like.

As shown by reference number 520, recommendation platform 230 may receive cross-industry and/or multi-domain data related to customer acquisition. For example, recommendation platform 230 may receive data that identifies a manner in which other organizations obtain customers, trends related to customer acquisition, such as the types of healthcare services that customers are consuming from other healthcare organizations or customer acquisition rates of other healthcare organizations, and/or the like.

In some implementations, cross-industry and/or multi-domain data may include data from multiple industries, including industries different from an industry that the organization being analyzed operates within. For example, in implementation 500, although recommendation platform 230 is analyzing an organization in, for example, healthcare, cross-industry and/or multi-domain data may include data related to customer acquisition in a retail industry, customer acquisition in a technology industry, and/or the like.

As shown by reference number 525, recommendation platform 230 may process the data using one or more techniques. For example, recommendation platform 230 may process the data using natural language processing, machine learning, and/or the like, as described elsewhere herein.

As shown in FIG. 5B, and by reference number 530, recommendation platform 230 may perform an analysis of the data using an organization operating model. Reference number 535 shows an example of an organization operating model that recommendation platform 230 may use to analyze an organization. For example, the organization operating model may include a customer channel functional area that includes telephone and web and/or virtual as sub-areas of the customer channel functional areas.

As shown by reference number 540, when analyzing the data, recommendation platform 230 may determine that the cross-industry and/or multi-domain data indicates a trend toward web and/or virtual acquisition of customers (e.g., that organizations are acquiring an increasing percentage of customers via web and/or virtual channels), and that top performing organizations (e.g., regardless of industry) obtain 50 percent (50%) of customers via web and/or virtual channels. This permits recommendation platform 230 to identify a deficiency related to customer-acquisition of the organization being analyzed relative to other organizations in the same or a different industry as the organization being analyzed.

As shown by reference number 545, recommendation platform 230 may analyze the data to determine a percentage of customers of the organization that are acquired via each channel of the organization (e.g., historical percentages). For example, recommendation platform 230 may determine that the organization acquires 35 percent (35%) of the organization's customers via telephone and 10 percent (10%) via a web and/or virtual channel.

As further shown by reference number 545, and by the shaded box, recommendation platform 230 may determine that the organization is underperforming relative to other organizations with respect to acquiring customers via a web and/or virtual channel (e.g., based on analyzing the cross-industry and/or multi-domain data and determining that other organizations acquire 50 percent of customers via a web and/or virtual channel). In this case, recommendation platform 230 may identify a deficiency related to customer acquisition of the organization based on the organization failing to acquire 50 percent of the organizations customers via a web and/or virtual channel.

As shown in FIG. 5C, and by reference number 550, recommendation platform 230 may perform an action related to increasing web and/or virtual customer acquisitions. For example, as shown by reference number 555, recommendation platform 230 may send a message to client device 210 (e.g., of a customer support representative) to cause the customer support representative to direct prospective customers to a web and/or virtual channel. Additionally, or alternative, and as another example, recommendation platform 230 may send a set of instructions to an interactive voice response (IVR) system to prevent sign ups via telephone (e.g., redirect customers to another channel) after the organization has acquired a threshold quantity of new customers via telephone.

As shown by reference number 560, recommendation platform 230 may use a knowledge base to perform big data analytics and/or machine learning using data from performing the analysis, managing process and/or operations implementation, and/or the like.

In some implementations, recommendation platform 230 may perform big data analytics to identify trends among multiple healthcare organizations, thereby enabling recommendation platform 230 to identify new and/or different deficiencies. Additionally, or alternatively, recommendation platform 230 may use machine learning to improve an accuracy of identifying a deficiency by using information related to identified deficiencies for multiple healthcare organizations.

As indicated above, FIGS. 5A-5C are provided merely as an example. Other examples are possible and may differ from what was described with regard to FIGS. 5A-5C.

Figure 6A:
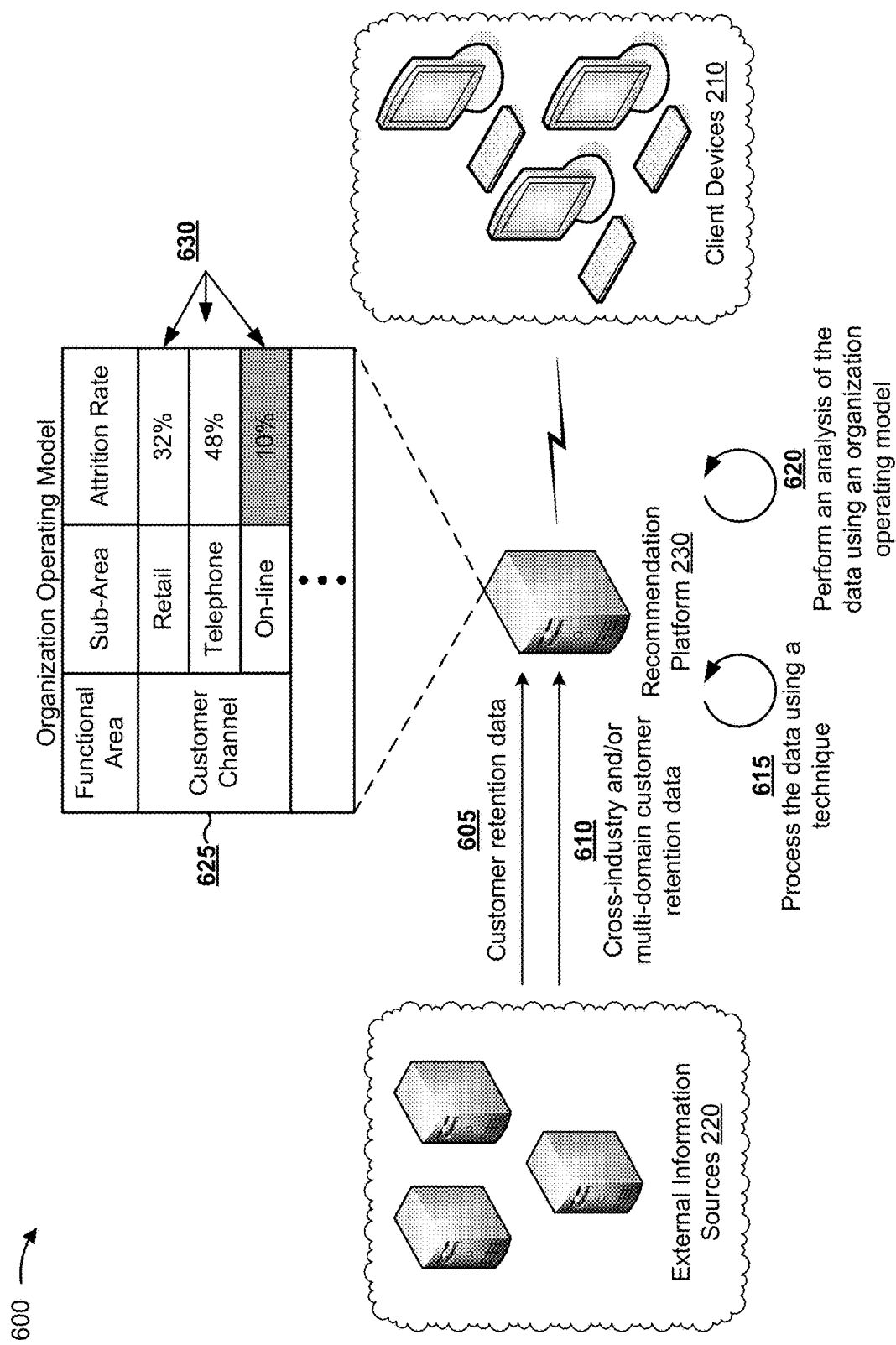
FIGS. 6A and 6B are diagrams of an example implementation relating to the example process shown in FIG. 4.
Figure 6B:
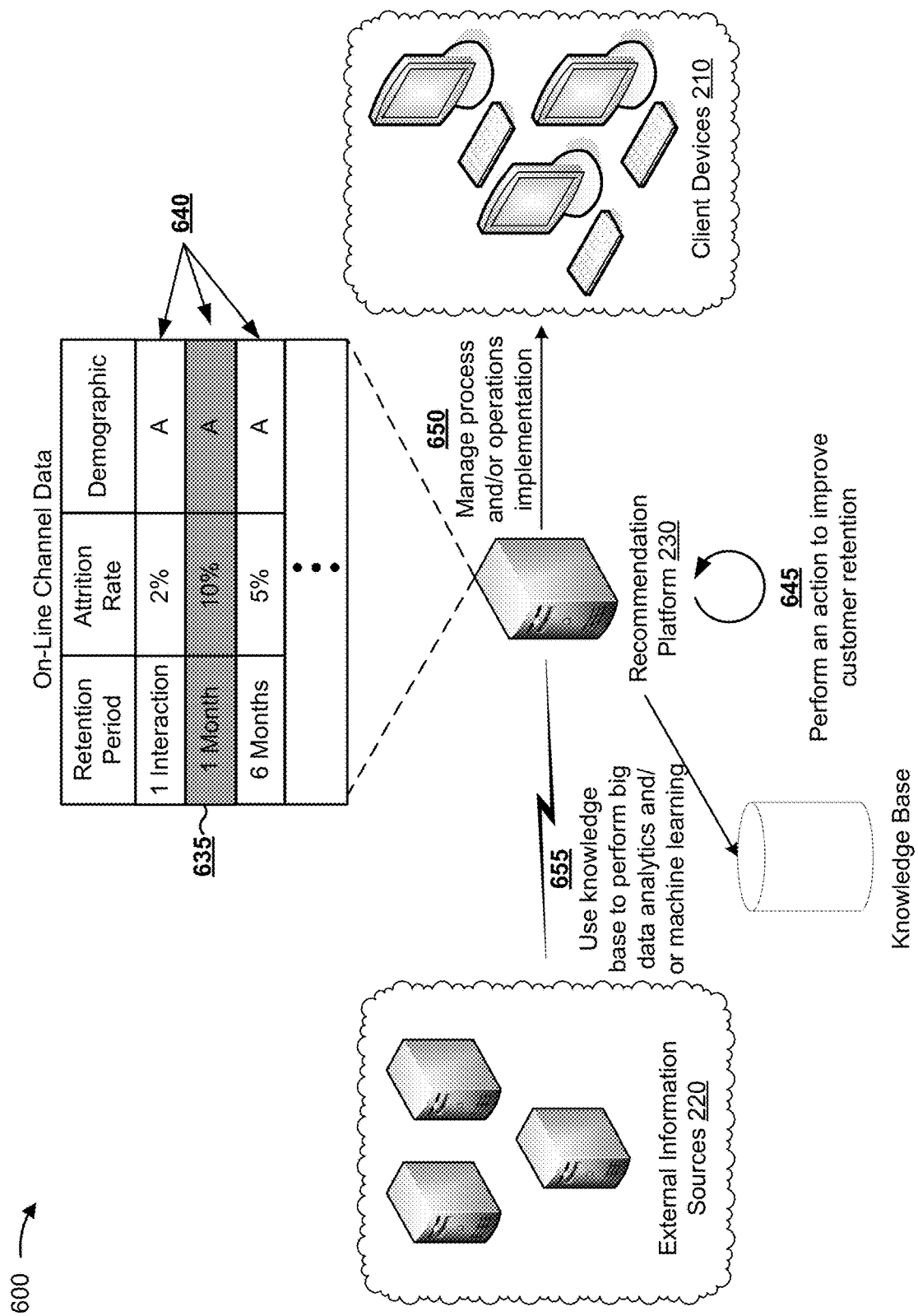

FIGS. 6A and 6B are diagrams of an example implementation 600 relating to example process 400 shown in FIG. 4. FIGS. 6A and 6B show an example of automatic analysis of process and/or operations data for channel optimization. As shown in FIGS. 6A and 6B, example implementation 600 may include client devices 210, external information sources 220, and recommendation platform 230.

As shown in FIG. 6A, and by reference number 605, recommendation platform 230 may receive, from external information sources 220, customer retention data related to a manner in which an organization retains customers. For example, the data may identify operations that the organization uses to retain customers, an attrition rate of customers from various channels of the organization (e.g., retail customers, telephone customers, on-line customers, etc.), and/or the like. As shown by reference number 610, recommendation platform 230 may receive cross-industry and/or multi-domain data related to customer retention. For example, recommendation platform 230 may receive data that identifies a manner in which other organizations retain customers, cross-industry trends related to customer retention, such as the types of operations that organizations are using to retain customers, and/or the like.

As shown by reference number 615, recommendation platform 230 may process the data using one or more techniques. For example, recommendation platform 230 may process the data using natural language processing, machine learning, and/or the like, as described elsewhere herein.

As shown by reference number 620, recommendation platform 230 may perform an analysis on the data using an organization operating model. Reference number 625 shows an example of an organization operating model that recommendation platform 230 may use to analyze an organization. For example, the organization operating model may include a customer channel functional area related to channels via which customers interact with the organization, such as to purchase a product or a service. Continuing with the previous example, the organization operating model may include retail, telephone, and on-line as sub-areas of the customer channel functional area.

As shown by reference number 630, when performing the analysis, recommendation platform 230 may identify an attrition rate for customers of each customer channel. For example, recommendation platform 230 may determine that the retail channel of the organization has a 35 percent attrition rate (e.g., meaning that 35 percent of retail customers have ceased using the retail channel during a time period), that the telephone channel of the organization has a 48 percent attrition rate, and that the on-line channel of the organization has a 10 percent attrition rate.

As further shown by reference number 630, recommendation platform 230 may determine that a negative 10 percent attrition rate for an on-line channel satisfies a threshold, as indicated by the shaded box. For example, recommendation platform 230 may have determined that other organizations have a five percent attrition rate for an on-line channel and that the 10 percent attrition rate of the organization being analyzed is greater than the five percent attrition rate of other organizations, thereby indicating a deficiency related to customer attrition via an on-line channel.

As shown by reference number 635, recommendation platform 230 may perform an analysis of customer attrition of an on-line channel in a more detailed manner. For example, recommendation platform 230 may analyze attrition rates for various retention periods and/or for different demographics. As shown by reference number 640, and as an example, recommendation platform 230 may determine that for an on-line channel of the organization being analyzed, demographic A has a two percent (2%) attrition rate after one interaction (e.g., one purchase), that demographic A has a 10 percent attrition rate after one month, and that demographic A has a five percent attrition rate after six months. As further shown by reference number 640, recommendation platform 230 may identify a deficiency related to the attrition rate of demographic A after one month (e.g., as shown by the shaded box).

As shown by reference number 645, recommendation platform 230 may perform an action to improve customer retention (e.g., generate a recommendation, send a message, schedule a meeting, etc., to improve capabilities of the organization). As shown by reference number 650, recommendation platform 230 may manage implementation of a process and/or operations (e.g., based on the analysis and/or action). As shown by reference number 655, recommendation platform 230 may use a knowledge base to perform big data analytics and/or machine learning.

As indicated above, FIGS. 6A and 6B are provided merely as an example. Other examples are possible and may differ from what was described with regard to FIGS. 6A and 6B.

Figure 7A:
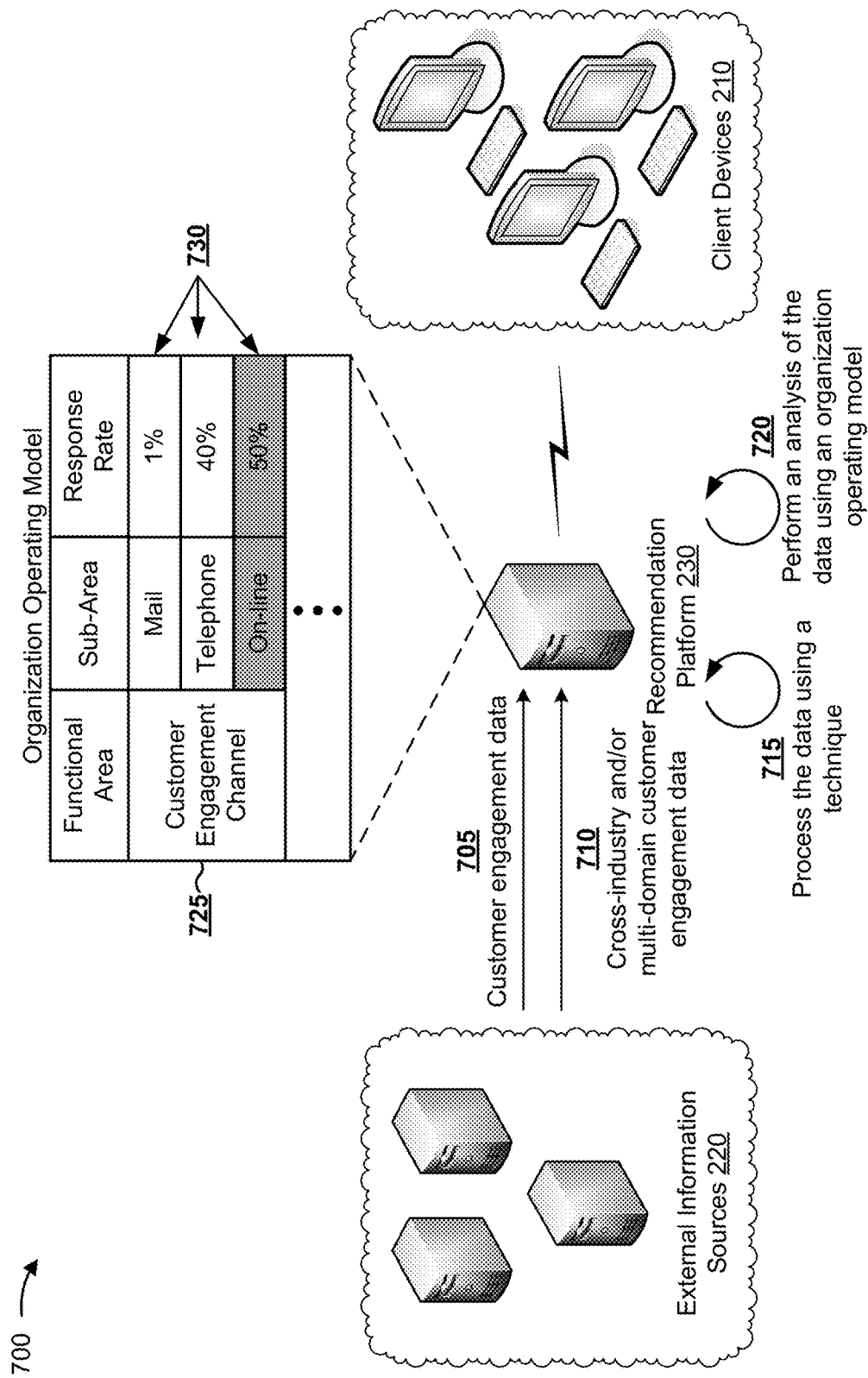
FIGS. 7A and 7B are diagrams of an example implementation relating to the example process shown in FIG. 4.
Figure 7B:
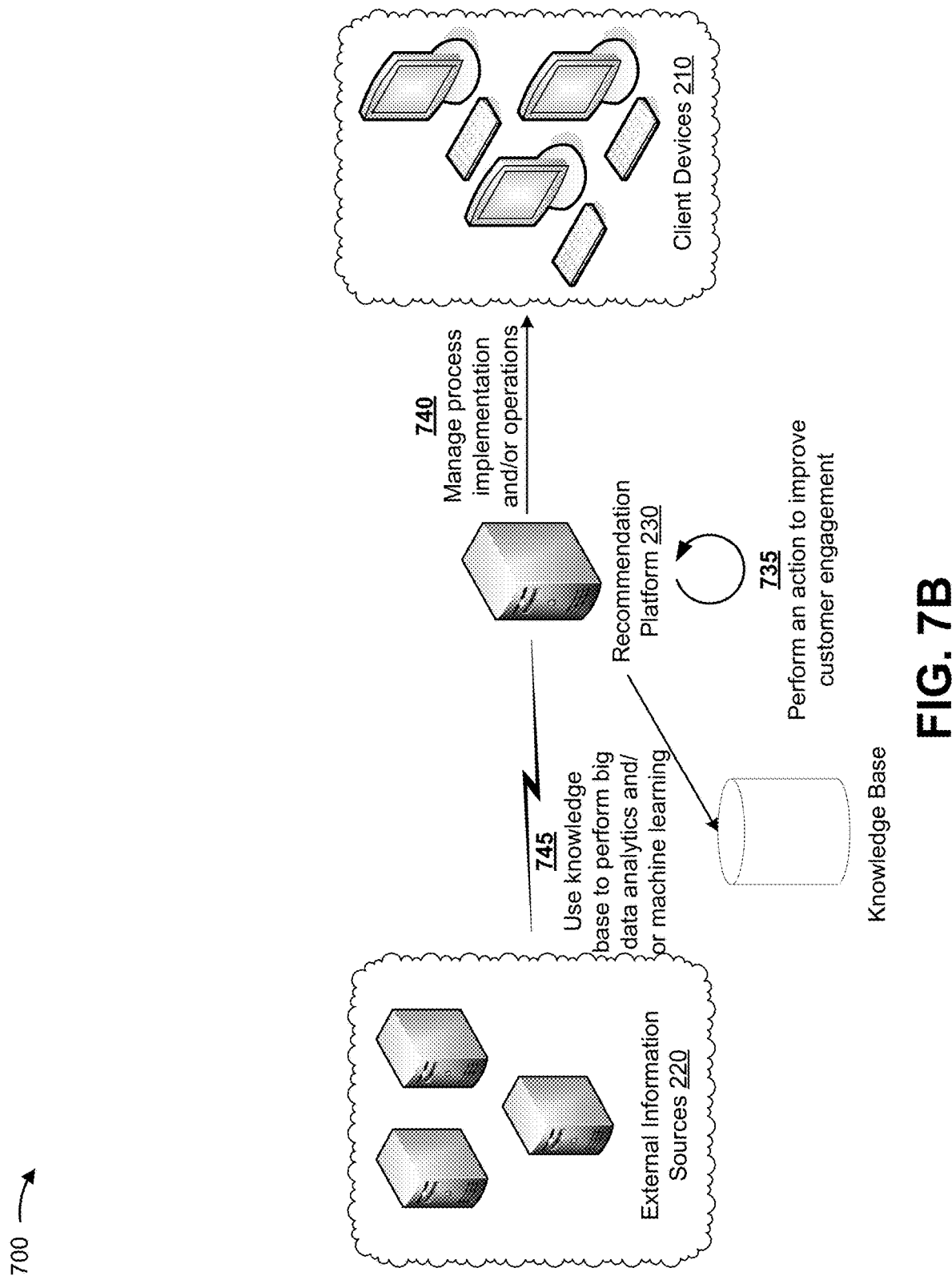

FIGS. 7A and 7B are diagrams of an example implementation 700 relating to example process 400 shown in FIG. 4. FIG. 4 shows an example of automatic analysis of process and/or operations data for channel optimization. As shown in FIGS. 7A and 7B, example implementation 700 includes client devices 210, external information sources 220, and recommendation platform 230.

As shown in FIG. 7A, and by reference number 705, recommendation platform 230 may receive, from external information sources 220, customer engagement data related to a manner in which an organization engages customers. For example, the data may identify operations that the organization uses to engage customers (e.g., survey, email, telephone, in-person visit, etc.), a response rate of customers to various types of customer engagements, and/or the like. As shown by reference number 710, recommendation platform 230 may receive cross-industry and/or multi-domain data related to customer engagement. For example, recommendation platform 230 may receive data that identifies a manner in which other organizations engage customers, cross-industry trends related to customer engagement, such as the types of operations that organizations are using to engage customers, and/or the like.

As shown by reference number 715, recommendation platform 230 may process the data using one or more techniques. For example, recommendation platform 230 may process the data using natural language processing, machine learning, and/or the like, as described elsewhere herein.

As shown by reference number 720, recommendation platform 230 may perform an analysis of the data using an organization operating model. Reference number 725 shows an example of an organization operating model that recommendation platform 230 may use to analyze an organization. For example, the organization operating model may include a customer engagement channel functional area related to channels via which an organization engages with customers, such as to obtain information related to an experience of the customer, promotions offered to existing customers, and/or the like. Continuing with the previous example, the organization operating model may include mail, telephone, and on-line as sub-areas of the customer engagement channel functional area.

As shown by reference number 730, recommendation platform 230 may determine response rates for various customer engagement channels. For example, recommendation platform 230 may determine that a mail customer engagement channel has a one percent (1%) response rate, that a telephone customer engagement channel has a 40 percent (40%) response rate, and that an on-line customer engagement channel has a 50 percent (50%) response rate. As further shown by reference number 730, recommendation platform 230 may determine that a response rate fails to satisfy a threshold, as shown by a shaded box. For example, recommendation platform 230 may use the cross-industry and/or multi-domain data to determine that the response rate for the on-line customer engagement channel is less than a response rate for an on-line channel of other organizations.

As shown by reference number 735, recommendation platform 230 may perform an action to improve customer engagement (e.g., generate a recommendation, send a message, schedule a meeting, etc. to improve operations of the organization related to customer engagement). As shown by reference number 740, recommendation platform 230 may manage implementation of a process and/or operations (e.g., based on the analysis and/or action). As shown by reference number 745, recommendation platform 230 may use a knowledge base to perform big data analytics and/or machine learning.

As indicated above, FIGS. 7A and 7B are provided merely as an example. Other examples are possible and may differ from what was described with regard to FIGS. 7A and 7B. In addition, although example implementations 500 through 700 were described as separate examples, example implementations 500 through 700 can occur concurrently.

Figure 8A:
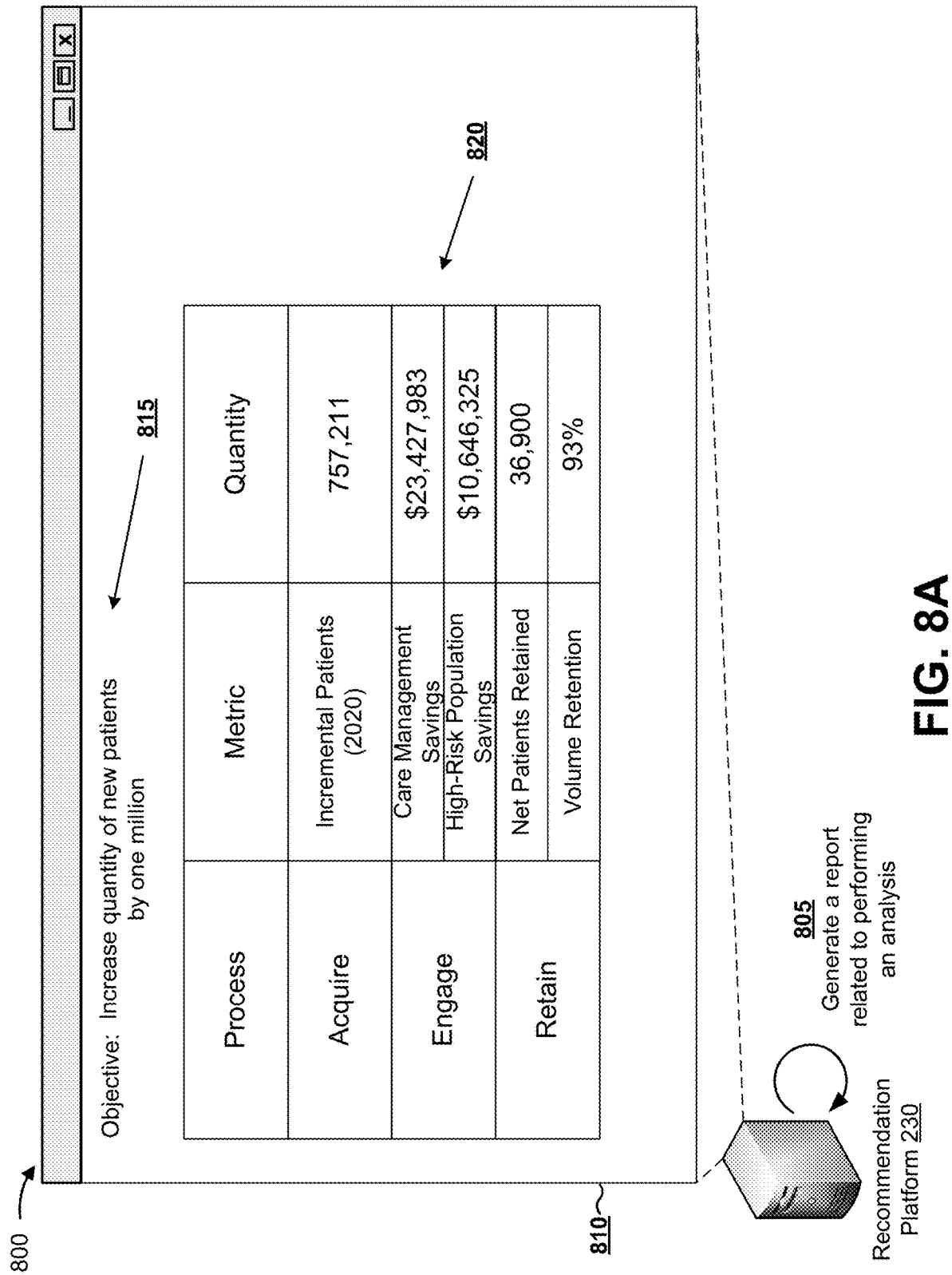
FIGS. 8A and 8B are diagrams of an example implementation relating to the example process shown in FIG. 4.
Figure 8B:
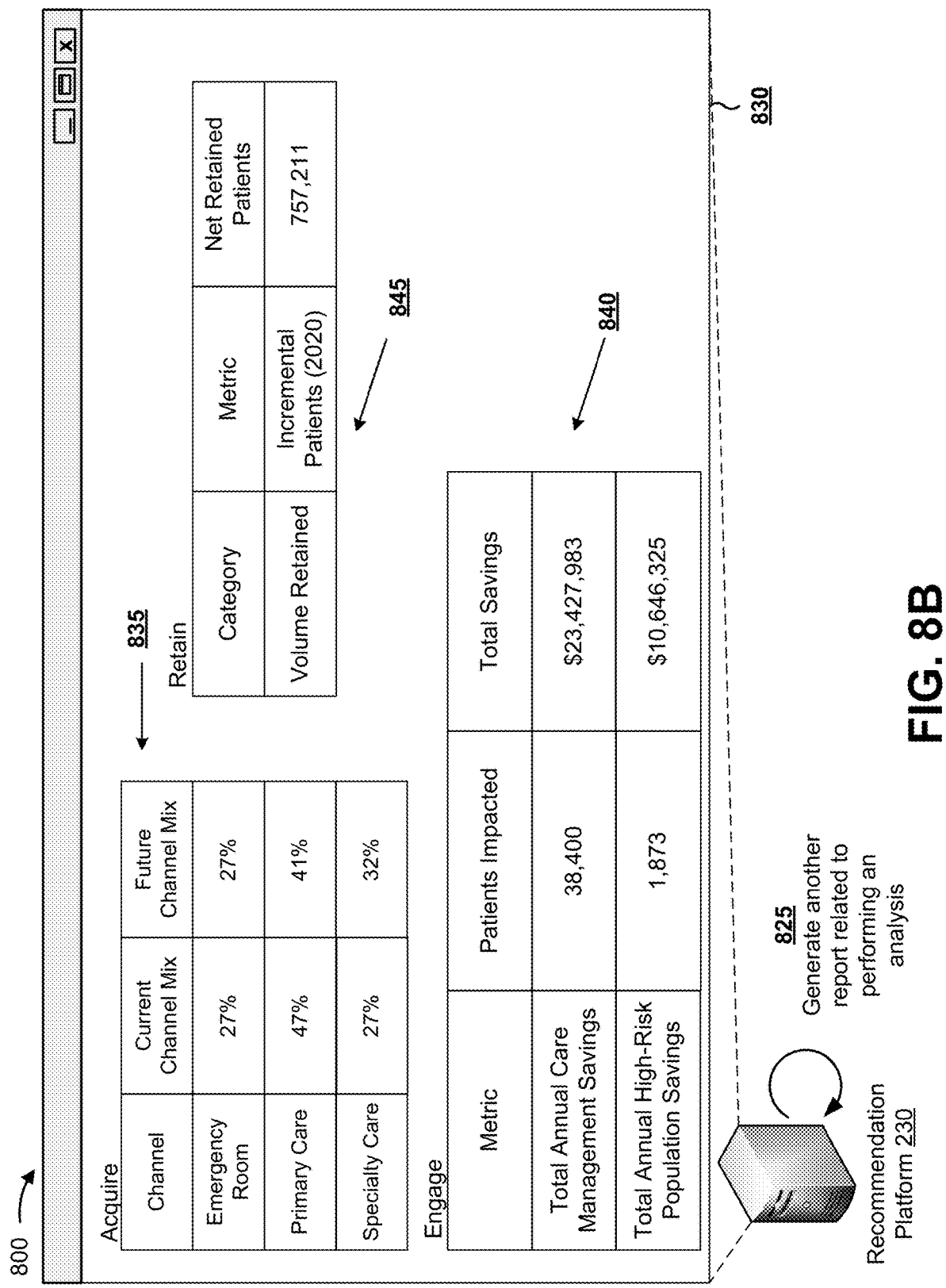

FIGS. 8A and 8B are diagrams of an example implementation 800 relating to example process 400 shown in FIG. 4. FIGS. 8A and 8B show example outputs that recommendation platform 230 may generate. In some implementations, the outputs may relate to an analysis that recommendation platform 230 has performed.

As shown in FIG. 8A, and by reference number 805, recommendation platform 230 may generate a report related to performing an analysis. For example, recommendation platform 230 may generate the report shown by reference number 810. As shown by reference number 815, the report may include information that identifies an objective for an analysis that recommendation platform 230 performs. For example, when performing the analysis, recommendation platform 230 may attempt to determine whether a healthcare organization can increase a quantity of new patients by one million, a manner in which the healthcare organization can increase a quantity of new patients by one million, and/or the like.

As shown by reference number 820, the report may include information identifying a predicted value of metrics related to the healthcare organization if the healthcare organization implements recommendations generated by recommendation platform 230. For example, if the healthcare organization implements recommendations that recommendation platform 230 generates, then the healthcare organization may acquire 757,211 new patients and/or retain 93 percent (93%) of existing patients.

As shown in FIG. 8B, and by reference number 825, recommendation platform 230 may generate another report related to performing an analysis. For example, recommendation platform 230 may generate the report shown by reference number 830. As shown by reference number 835, the report may include information related to an analysis of patient acquisition operations of a healthcare organization. For example, the report may indicate that if the healthcare organization implements recommendations that recommendation platform 230 generated, then the healthcare organization may have a different channel combination for patients. For example, if the healthcare organization implements recommendations that recommendation platform 230 generates, then the healthcare organization may acquire 41 percent (41%) of new patients via a primary care channel rather than 47 percent (47%) of new patients.

As shown by reference number 840, the report may include information related to an analysis of patient engagement. For example, if the healthcare organization implements a recommendation that recommendation platform 230 has generated, then the healthcare organization may engage 38,400 patients and save 23,427,983 dollars ($23,427,983). As shown by reference number 845, the report may include information related to an analysis of retaining patients. For example, if the healthcare organization implements a recommendation that recommendation platform 230 has generated, then the healthcare organization may retain a net of 757,211 patients.

In this way, recommendation platform 230 may generate a report related to performing an analysis.

Implementations described herein provide a recommendation platform that is capable of receiving data associated with a performance of a process of an organization and/or operations of the organization related to customers of the organization, analyzing the data to identify a deficiency related to the performance and/or a manner in which the performance can be improved, and/or automatically performing an action to positively impact the deficiency and/or to improve the performance.

In this way, the recommendation platform increases an efficiency of analyzing a process of an organization and/or operations of the organization. In addition, this improves an accuracy of a result and/or output of a process, thereby conserving processing resources that would otherwise be consumed due to inaccurate results and/or outputs. Further, this improves performance of a process and/or operations of an organization, thereby conserving processing resources and/or computing resources of devices used to implement the process and/or the operations.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more processors to:
receive data associated with customers, a customer-related process, or customer-related operations of an organization,
the data being received from an external information source;
process the data, after receiving the data, using at least natural language processing;
map the data to an organization operating model based on the processing of the data using the at least natural language processing,
the organization operating model to be used to identify at least one of:
a trend related to the customers of the organization, or
a deficiency related to the customer-related process or the customer-related operations, and
wherein the trend or the deficiency is associated with at least one of storage capacity, installed software, or processing capabilities of devices used to perform the trend, the customer-related process, or the customer-related operations;
perform an analysis of the data using the organization operating model and based on mapping the data to the organization operating model;
identify a customer-channel combination of the organization based on performing the analysis,
the customer-channel combination being a channel, for communicating with the customers, via which the organization acquires, engages, or retains the customers;
determine, based on the analysis, using the organization operating model, and for a plurality of devices used to perform the customer-related process or the customer-related operations via the customer-channel combination, that at least one of storage capacity, installed software, or processing capabilities of the plurality of devices satisfies a threshold;
generate, based on the analysis and based on the at least one of the storage capacity, the installed software, or the processing capabilities of the plurality of devices satisfying the threshold, a score indicating a measure of severity, priority, or predicted impact associated with an action to be taken with respect to the plurality of devices;
determine to prioritize the action based on the score being greater than another score associated with another trend or another deficiency associated with the at least one of storage capacity, installed software, or processing capabilities of the plurality of devices; and
perform, based on the action being prioritized, the action to positively impact performance of the customer-related process, to positively impact the customer-related operations, or to modify the customer-channel combination of the organization,
wherein the one or more processors, when performing the action, are to:
bring an additional device online,
bring a particular device, of the plurality of devices, offline,
install or activate additional software associated with the plurality of devices, or
update the installed software.

2. The device of claim 1, where the one or more processors are further to:
determine a percentage of the customers that the organization acquires, engages, or retains via various channels; and
where the one or more processors, when identifying the customer-channel combination, are to:
identify the customer-channel combination based on determining the percentage of the customers that the organization acquires, engages, or retains via the various channels.

3. The device of claim 1, where the one or more processors are further to:
generate an objective related to the customers, the customer-related process, or the customer-related operations; and
where the one or more processors, when performing the action, are to:
perform the action to permit the organization to satisfy the objective.

4. The device of claim 1, where the one or more processors are further to:
determine an additional trend related to other customer-channel combinations of other organizations based on performing the analysis of the data;
determine a type of customer that the organization can acquire, retain, or engage based on the additional trend and the customer-channel combination; and
where the one or more processors, when performing the action, are to:
perform the action based on determining the type of customer that the organization can acquire, retain, or engage.

5. The device of claim 1, where the one or more processors are further to:
determine a future customer-channel combination of the organization; and
where the one or more processors, when performing the action, are to:
perform the action based on determining the future customer-channel combination.

6. The device of claim 1, where the one or more processors are further to:
receive information identifying an objective of the organization related to the customer-channel combination, the customers, the customer-related process, or the customer-related operations of the organization; and
determine whether the organization can satisfy the objective based on performing the analysis.

7. The device of claim 1, where the one or more processors are further to:
identify, based on the at least one of the storage capacity, the installed software, or the processing capabilities of the plurality of devices satisfying the threshold, that the deficiency is related to the plurality of devices; and
where the one or more processors, when performing the action, are to:
perform the action based on identifying that the deficiency is related to the plurality of devices.

8. A method, comprising:
receiving, by a device, data associated with customers, a customer-related process, or customer-related operations of an organization;

processing, by the device and using at least natural language processing, the data after receiving the data;

mapping, by the device, the data to an organization operating model based on the processing of the data using the at least natural language processing, the organization operating model to be used to perform an analysis of the data to identify at least one of:

a deficiency related to the customers, the customer-related process, or the customer-related operations of the organization, or a first manner in which to improve a customer-channel combination, the customer-related process, or the customer-related operations, and wherein the deficiency, or the first manner in which to improve the customer-channel combination, the customer-related process, or the customer-related operations, is associated with at least one of storage capacity, installed software, or processing capabilities of devices used to perform the customer-channel combination, the customer-related process, or the customer-related operations;

performing, by the device, the analysis of the data using the organization operating model and based on mapping the data to the organization operating model, the organization operating model to be used to identify the deficiency or the first manner in which to improve the customer-channel combination, the customer-related process, or the customer-related operations;

identifying, by the device, the customer-channel combination of the organization based on performing the analysis, the customer-channel combination being a channel, for communicating with the customers, via which the organization acquires, engages, or retains the customers;

determining, by the device, using the organization operating model, based on the analysis, and for a plurality of devices used to perform the customer-related process or the customer-related operations via the customer-channel combination, that at least one of storage capacity, installed software, or processing capabilities of the plurality of devices satisfies a threshold;

generating, by the device, based on the analysis, and based on the at least one of the storage capacity, the installed software, or the processing capabilities of the plurality of devices satisfying the threshold, a score indicating a measure of severity, priority, or predicted impact associated with an action to be taken with respect to the plurality of devices;

determining, by the device, to prioritize the action based on the score being greater than another score associated with another action to be taken with respect to the plurality of devices; and performing, by the device and based on the action being prioritized, the action to positively impact performance of the customer-related process, to positively impact the customer-related operations, or to modify the customer-channel combination of the organization, wherein performing the action comprises:
bringing an additional device online,
bringing a particular device, of the plurality of devices, offline,
installing or activating additional software associated with the plurality of devices, or
updating the installed software.

9. The method of claim 8, further comprising:
determining a value for the customer-channel combination;
determining a future value for the customer-channel combination using other data associated with another organization; and
where performing the action comprises:
performing the action based on determining the future value of the customer-channel combination,
the action to positively impact the future value of the customer-channel combination.

10. The method of claim 8, further comprising:
generating an objective related to the customers, the customer-related process, or the customer-related operations; and
where performing the analysis comprises:
performing the analysis to determine whether the organization can satisfy the objective.

11. The method of claim 8, further comprising:
generating an objective related to the customers, the customer-related process, or the customer-related operations of the organization;
determining a second manner in which the organization can satisfy the objective; and
where performing the action comprises:
performing the action based on determining the second manner in which the organization can satisfy the objective.

12. The method of claim 8, further comprising:
determining a value associated with an objective related to the customers, the customer-related process, or the customer-related operations;
determining whether the value satisfies another threshold; and
where performing the action comprises:
performing the action based on determining whether the value satisfies the other threshold.

13. The method of claim 8, further comprising:
identifying a trend related to the customer-channel combination of the organization or another customer-channel combination of another organization,
the trend indicating a future customer-channel combination of the organization,
the trend being identified using cross-industry data; and
where performing the action comprises:
performing the action based on identifying the trend.

14. The method of claim 8, where performing the action further comprises:
generating a recommendation to modify the customer-channel combination,
the customer-channel combination including:
a web channel,
a virtual channel,
a telephone channel, or
a retail channel.

15. A non-transitory computer-readable medium storing instructions, the instructions comprising:
one or more instructions that, when executed by one or more processors, cause the one or more processors to:
receive data associated with customers, a customer-related process, or customer-related operations of an organization,
the data being received from an external information source;
process the data using, after receiving the data, at least natural language processing;

map the data to an organization operating model based on the processing of the data using the at least natural language processing,
  the organization operating model to be used to identify at least one of:
    a trend related to the customers of the organization, or
    a deficiency related to the customer-related process or the customer-related operations, and
  wherein the trend or the deficiency is associated with at least one of storage capacity, installed software, or processing capabilities of devices used to perform the trend, the customer-related process, or the customer-related operations;
perform an analysis of the data using the organization operating model and based on mapping the data to the organization operating model;
identify a customer-channel combination of the organization based on performing the analysis,
  the customer-channel combination being a channel, for communicating with the customers, via which the organization acquires, engages, or retains the customers;
determine, based on the analysis, using the organization operating model, and for a plurality of devices used to perform the customer-related process or the customer-related operations via the customer-channel combination, that at least one of storage capacity, installed software, or processing capabilities of the plurality of devices satisfies a threshold;
generate, based on the analysis and based on the at least one of the storage capacity, the installed software, or the processing capabilities of the plurality of devices satisfying the threshold, a score indicating a measure of severity, priority, or predicted impact associated with an action to be taken with respect to the plurality of devices;
determine to prioritize the action based on the score being greater than another score associated with another trend or another deficiency; and
perform, based on the action being prioritized, the action to positively impact performance of the customer-related process, to positively impact the customer-related operations, or to modify the customer-channel combination of the organization,
  where the one or more instructions, that cause the one or more processors to perform the action, cause the one or more processors to:
    bring an additional device online,
    bring a particular device, of the plurality of devices, offline,
    install or activate additional software associated with the plurality of devices, or
    update the installed software.

16. The non-transitory computer-readable medium of claim 15, where the one or more instructions, when executed by the one or more processors, further cause the one or more processors to:
  determine a percentage of the customers that the organization acquires, engages, or retains via various channels; and
  where the one or more instructions, that cause the one or more processors to identify the customer-channel combination, cause the one or more processors to:
    identify the customer-channel combination based on determining the percentage of the customers that the organization acquires, engages, or retains via the various channels.

17. The non-transitory computer-readable medium of claim 15, where the one or more instructions, when executed by the one or more processors, further cause the one or more processors to:
  generate an objective related to the customers, the customer-related process, or the customer-related operations; and
  where the one or more instructions, that cause the one or more processors to perform the action, further cause the one or more processors to:
    perform the action to permit the organization to satisfy the objective.

18. The non-transitory computer-readable medium of claim 15, where the one or more instructions, when executed by the one or more processors, further cause the one or more processors to:
  determine another trend related to other customer-channel combinations of other organizations based on performing the analysis of the data;
  determine a type of customer that the organization can acquire, retain, or engage based on the other trend and the customer-channel combination; and
  where the one or more instructions, that cause the one or more processors to perform the action, further cause the one or more processors to:
    perform the action based on determining the type of customer that the organization can acquire, retain, or engage.

19. The non-transitory computer-readable medium of claim 15, where the one or more instructions, when executed by the one or more processors, further cause the one or more processors to:
  determine a future customer-channel combination of the organization; and
  where the one or more instructions, that cause the one or more processors to perform the action, further cause the one or more processors to:
    perform the action based on determining the future customer-channel combination.

20. The non-transitory computer-readable medium of claim 15, where the one or more instructions, when executed by the one or more processors, further cause the one or more processors to:
  receive information identifying an objective of the organization related to the customer-channel combination, the customers, the customer-related process, or the customer-related operations of the organization; and
  determine whether the organization can satisfy the objective based on performing the analysis.

* * * * *